US009701724B2

(12) United States Patent
Yokogawa et al.

(10) Patent No.: US 9,701,724 B2
(45) Date of Patent: Jul. 11, 2017

(54) VACCINE FOR PREVENTING PORCINE EDEMA DISEASE

(71) Applicants: The Chemo-Sero-Therapeutic Research Institute, Kumamoto-shi (JP); Jectas Innovators Company Limited, Naha-shi (JP)

(72) Inventors: Kenji Yokogawa, Kumamoto (JP); Takashi Waki, Kumamoto (JP); Yoko Honda, Kumamoto (JP); Hirotaka Uefuji, Okinawa (JP); Tomomitsu Sewaki, Okayama (JP); Takeshi Arakawa, Okinawa (JP); Tetsuya Harakuni, Okinawa (JP); Takeshi Miyata, Kagoshima (JP)

(73) Assignees: The Chemo-Sero-Therapeutic Research Institute, Kumamoto-shi (JP); Jectas Innovators Company Limited, Naha-shi (JP)

( * ) Notice: Subject to any disclaimer, the term of this patent is extended or adjusted under 35 U.S.C. 154(b) by 0 days.

(21) Appl. No.: 14/437,666

(22) PCT Filed: Oct. 18, 2013

(86) PCT No.: PCT/JP2013/078305

§ 371 (c)(1),
(2) Date: Apr. 22, 2015

(87) PCT Pub. No.: WO2014/065210

PCT Pub. Date: May 1, 2014

(65) Prior Publication Data

US 2015/0361142 A1 Dec. 17, 2015

(30) Foreign Application Priority Data

Oct. 22, 2012 (JP) ................................ 2012-233224

(51) Int. Cl.
*A61K 39/00* (2006.01)
*A61K 39/02* (2006.01)
(Continued)

(52) U.S. Cl.
CPC ........ *C07K 14/245* (2013.01); *A61K 39/0005* (2013.01); *A61K 39/0258* (2013.01);
(Continued)

(58) Field of Classification Search
None
See application file for complete search history.

(56) References Cited

U.S. PATENT DOCUMENTS

2012/0100165 A1* 4/2012 Arakawa .............. A61K 39/015 424/185.1

FOREIGN PATENT DOCUMENTS

JP 2008-050344 A 3/2008
WO WO 0075345 * 12/2000 ............. C12N 15/62
(Continued)

OTHER PUBLICATIONS

Ran et al., (Vet. Microbiol. 2008. 127(1-2):209-15.).*
(Continued)

*Primary Examiner* — Ja'Na Hines
(74) *Attorney, Agent, or Firm* — Oblon, McClelland, Maier & Neustadt, L.L.P.

(57) ABSTRACT

A purpose is to provide a vaccine which can prevent porcine edema disease in farms where porcine edema disease is anticipated. Meeting this purpose is a vaccine that is a fusion protein in which Stx2eB and a polypeptide having a coiled-coil forming unit are joined or a multimer of the fusion protein, and by immunizing pigs with this vaccine, it is possible to induce potent neutralizing antibodies and to defend against the onset of porcine edema disease.

20 Claims, 3 Drawing Sheets

N: amino-terminus C: carboxyl-terminus $H_6$: His-tag

(51) Int. Cl.
*A61K 39/38* (2006.01)
*A61K 51/00* (2006.01)
*C07K 14/245* (2006.01)
*A61K 39/108* (2006.01)
*C07K 16/12* (2006.01)
*C07K 14/435* (2006.01)
*C07K 16/18* (2006.01)

(52) U.S. Cl.
CPC ........ *C07K 14/435* (2013.01); *C07K 16/1232* (2013.01); *C07K 16/18* (2013.01); *A61K 2039/53* (2013.01); *A61K 2039/552* (2013.01); *C07K 2317/76* (2013.01); *C07K 2319/21* (2013.01); *C07K 2319/55* (2013.01); *C07K 2319/73* (2013.01)

(56) References Cited

FOREIGN PATENT DOCUMENTS

| | | | | |
|---|---|---|---|---|
| WO | WO 2009133885 | * | 11/2009 | C12N 15/09 |
| WO | WO 2010/092963 | * | 8/2010 | A61K 39/385 |
| WO | WO 2010/092963 A1 | | 8/2010 | |

OTHER PUBLICATIONS

International Search Report issued Dec. 3, 2013 in PCT/JP2013/078305 filed Oct. 18, 2013.

Xue Qin Ran, et al., "The immunogenicity of fusion protein linking the carboxyl terminus of the B subunit of Shiga toxin 2 to the B subunit of *E.coli* heat-labile enterotoxin" Veterinary Microbiology, vol. 127, No. 1-2, Feb. 5, 2008, 7 Pages.

Takeshi Matsui, et al., "Production of double repeated B subunit of Shiga toxin 2e at high levels in transgenic lettuce plants as vaccine material for porcine edema disease", Transgenic Res., vol. 20, No. 4, Aug. 2011, 14 Pages.

Xinzhen Yang, et al., "Improved Elicitation of Neutralizing Antibodies against Primary Human Immunodeficiency Viruses by Soluble Stabilized Envelope Glycoprotein Trimers" Journal of Virology, Feb. 2001, vol. 75, No. 3, 8 Pages.

Piyali Saha, et al., Designed Cyclic Permutants of HIV-1 gp120: Implications for Envelope Trimer Structure and Immunogen Design, Biochemistry, vol. 51, No. 9, Mar. 6, 2012, 12 Pages.

S. Yu. Belitskaya, et al., "Design of Chimeric Proteins on the Basis of a Pentameric Superhelical Fragment of Human Cartilage Oligometric Matrix Protein: I. The Properties of a Hybrid Containing the Immunodominant Domain of the Circumsporozoite Protein of *Plasmodium falciparum*" Russian Journal of Bioorganic Chemistry, vol. 30, No. 1, 2004, 7 Pages.

Andrei N. Lupas, et al., "The Structure of α-Helical Coiled Coils" Advances in Protein Chemistry, vol. 70, 2005, 42 pages.

Extended European Search Report issued Jun. 9, 2016 in Patent Application No. 13848760.8.

Yukihiro Tamaki, et al., "Cholera Toxin B Subunit Pentamer Reassembled From *Escherichia Coli* Inclusion Bodies for Use in Vaccination" Vaccine, Elsevier, vol. 34, No. 10, XP029437445, Jan. 29, 2016, pp. 1268-1274.

Takeshi Miyata, et al., "Tricomponent Immunopotentiating System as a Novel Molecular Design Strategy for Malaria Vaccine Development" Infection and Immunity, American Society for Microbiology, vol. 79, No. 10, XP002679825, Oct. 1, 2011, pp. 4260-4275.

Sueyoshi, M., "Edema Disease with Diarrhea of Piglets (Enterotoxaemia by *Escherichia Coli* of Piglets)" Proc. Jpn. Pig Vet. Soc., No. 48, 2006, pp. 7-13.

David L. MacLeod, et al., "Immunization of Pigs with a Purified Shiga-Like Toxin II Variant Toxoid" Veterinary Microbiology, Elsevier Science Publishers, No. 29, 1991, pp. 309-318.

V. M. Gordon, et al., "An Enzymatic Mutant of Shiga-Like Toxin II Variant is a Vaccine Candidate for Edema Disease of Swine" Infection and Immunity, American Society for Microbiology, vol. 60, No. 2, 1992, pp. 485-490.

Tetsuya Harakuni, et al., "Heteropentameric Cholera Toxin B Subunit Chimeric Molecules Genetically Fused to a Vaccine Antigen Induce Systemic and Mucosal Immune Responses: a Potential New Strategy to Target Recombinant Vaccine Antigens to Mucosal Immune Systems" Infection and Immunity, American Society for Microbiology, vol. 73, No. 9, 2005, pp. 5654-5665.

* cited by examiner

Fig. 1

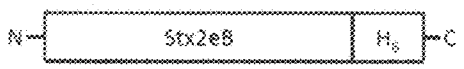

N: amino-terminus C: carboxyl-terminus $H_6$: His-tag

Fig. 2

N: amino-terminus N: carboxyl-terminus $(GP)_2GH_6(G_4S)_3$: linker
COMP: pentamer-forming domain of cartilage oligomeric matrix protein

Fig. 3

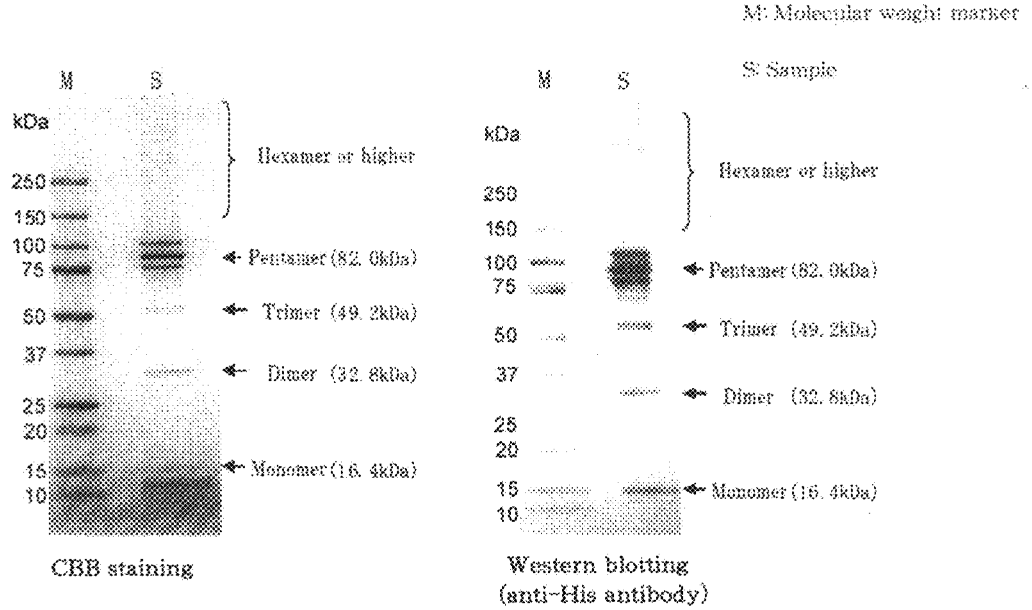

Fig. 4

N: amino-terminus C: carboxyl-terminus Linker 1: $(GP)_2GH_6(G_4S)_3$
COMP: pentamer-forming domain of cartilage oligomeric matrix protein
Linker 2: $(GP)_2G_4SH_6G_4S(GP)_2$ Domain Z: immunoglobulin-binding domain Z N: amino-terminus C: carboxyl-terminus $(GP)_2GH_6(G_4S)_3$: linker
CMP: trimer-forming domain of cartilage matrix protein

SEQUENCE LISTING

```
<160> NUMBER OF SEQ ID NOS: 36

<210> SEQ ID NO 1
<211> LENGTH: 264
<212> TYPE: DNA
<213> ORGANISM: Escherichia coli

<400> SEQUENCE: 1

atgaagaaga tgtttatagc ggttttattt gcattggttt ctgttaatgc aatggcggcg      60

gattgtgcta aaggtaaaat tgagttttcc aagtataatg aggataatac ctttactgtg     120

aaggtgtcag gaagagaata ctggacgaac agatggaatt tgcagccatt gttacaaagt     180

gctcagctga cagggatgac tgtaacaatc atatctaata cctgcagttc aggctcaggc     240

tttgcccagg tgaagtttaa ctga                                            264


<210> SEQ ID NO 2
<211> LENGTH: 270
<212> TYPE: DNA
<213> ORGANISM: Artificial Sequence
<220> FEATURE:
<223> OTHER INFORMATION: Synthetic nucleotide modified for E. coli and
      yeast expression

<400> SEQUENCE: 2

catatgaaaa aaatgtttat cgcggtgctg ttcgccttgg tgagcgttaa tgcgatggcc      60

gcggattgcg cgaaaggcaa aattgaattt tcgaaatata atgaagataa cacctttacc     120

gtgaaagtga gcggtcgcga atattggacc aatcgttgga atctgcagcc gttactgcaa     180
```

-continued

```
tcggcccagc tgaccggcat gaccgttacc attatcagca acacctgcag ctcgggcagt    240

ggttttgcgc aggtgaaatt caatctcgag                                     270


<210> SEQ ID NO 3
<211> LENGTH: 31
<212> TYPE: DNA
<213> ORGANISM: Artificial Sequence
<220> FEATURE:
<223> OTHER INFORMATION: Synthetic nucleotide containing the Nco I
      restriction enzyme recognition sequence

<400> SEQUENCE: 3

catgccatgg attgcgcgaa aggcaaaatt g                                    31


<210> SEQ ID NO 4
<211> LENGTH: 32
<212> TYPE: DNA
<213> ORGANISM: Artificial Sequence
<220> FEATURE:
<223> OTHER INFORMATION: Synthetic nucleotide containing the Xho I
      restriction enzyme recognition sequence

<400> SEQUENCE: 4

ccgctcgaga ttgaatttca cctgcgcaaa ac                                   32


<210> SEQ ID NO 5
<211> LENGTH: 76
<212> TYPE: PRT
<213> ORGANISM: Artificial Sequence
<220> FEATURE:
<223> OTHER INFORMATION: Synthetic peptide: Stx2eB-His
<220> FEATURE:
<221> NAME/KEY: DISULFID
<222> LOCATION: (3)..(56)
<223> OTHER INFORMATION: Intramolecular disulfide bond

<400> SEQUENCE: 5

Met Asp Cys Ala Lys Gly Lys Ile Glu Phe Ser Lys Tyr Asn Glu Asp
1               5                   10                  15

Asn Thr Phe Thr Val Lys Val Ser Gly Arg Glu Tyr Trp Thr Asn Arg
            20                  25                  30

Trp Asn Leu Gln Pro Leu Leu Gln Ser Ala Gln Leu Thr Gly Met Thr
        35                  40                  45

Val Thr Ile Ile Ser Asn Thr Cys Ser Ser Gly Ser Gly Phe Ala Gln
    50                  55                  60

Val Lys Phe Asn Leu Glu His His His His His His
65                  70                  75


<210> SEQ ID NO 6
<211> LENGTH: 231
<212> TYPE: DNA
<213> ORGANISM: Artificial Sequence
<220> FEATURE:
<223> OTHER INFORMATION: Synthetic nucleotide: Stx2eB-His

<400> SEQUENCE: 6

atggattgcg cgaaaggcaa aattgaattt tcgaaatata atgaagataa cacctttacc     60

gtgaaagtga gcggtcgcga atattggacc aatcgttgga atctgcagcc gttactgcaa    120

tcggcccagc tgaccggcat gaccgttacc attatcagca acacctgcag ctcgggcagt    180

ggttttgcgc aggtgaaatt caatctcgag caccaccacc accaccactg a             231
```

-continued

<210> SEQ ID NO 7
<211> LENGTH: 40
<212> TYPE: DNA
<213> ORGANISM: Artificial Sequence
<220> FEATURE:
<223> OTHER INFORMATION: Synthetic nucleotide containing the Mun I restriction enzyme recognition sequence

<400> SEQUENCE: 7
gcgccaattg gccaccatga ttaaattaaa atttggtgtt 40

<210> SEQ ID NO 8
<211> LENGTH: 88
<212> TYPE: DNA
<213> ORGANISM: Artificial Sequence
<220> FEATURE:
<223> OTHER INFORMATION: Synthetic nucleotide containing the Mun I restriction enzyme recognition sequence and (GP)2GH6 (EcoRI) H6 linker

<400> SEQUENCE: 8
ggcaattgtt aatgatggtg atggtgatgg aattcatggt gatggtgatg atgtccaggt 60
cctggaccat ttgccatact aattgcgg 88

<210> SEQ ID NO 9
<211> LENGTH: 45
<212> TYPE: DNA
<213> ORGANISM: Artificial Sequence
<220> FEATURE:
<223> OTHER INFORMATION: Synthetic nucleotide: (G4S)3 linker

<400> SEQUENCE: 9
ggcggtggcg gtagcggcgg tggcggtagc ggcggtggcg gtagc 45

<210> SEQ ID NO 10
<211> LENGTH: 165
<212> TYPE: DNA
<213> ORGANISM: Artificial Sequence
<220> FEATURE:
<223> OTHER INFORMATION: Synthetic nucleotide modified for E.coli and yeast expression

<400> SEQUENCE: 10
ggcggtgatc tggcgccgca gatgctgcgc gaactgcagg aaaccaacgc ggccctgcaa 60
gatgtgcgtg aactgctgcg ccagcaagtg aaagaaatta cctttctgaa aaataccgtt 120
atggaatgcg atgcgtgtgg catgcagccg gcccgtaccc cgggc 165

<210> SEQ ID NO 11
<211> LENGTH: 210
<212> TYPE: DNA
<213> ORGANISM: Artificial Sequence
<220> FEATURE:
<223> OTHER INFORMATION: Synthetic nucleotide modified for (G4S)3 linker and E. coli

<400> SEQUENCE: 11
ggcggtggcg gtagcggcgg tggcggtagc ggcggtggcg gtagcggcgg tgatctggcg 60
ccgcagatgc tgcgcgaact gcaggaaacc aacgcggccc tgcaagatgt gcgtgaactg 120
ctgcgccagc aagtgaaaga aattaccttt ctgaaaaata ccgttatgga atgcgatgcg 180
tgtggcatgc agccggcccg taccccgggc 210

<210> SEQ ID NO 12
<211> LENGTH: 30

-continued

<212> TYPE: DNA
<213> ORGANISM: Artificial Sequence
<220> FEATURE:
<223> OTHER INFORMATION: Synthetic nucleotide containing the Mun I restriction enzyme recognition sequence

<400> SEQUENCE: 12
gcgcaattgg gcggtggcgg tagcggcggt 30

<210> SEQ ID NO 13
<211> LENGTH: 31
<212> TYPE: DNA
<213> ORGANISM: Artificial Sequence
<220> FEATURE:
<223> OTHER INFORMATION: Synthetic nucleotide containing the EcoR I restriction enzyme recognition sequence

<400> SEQUENCE: 13
gcggaattcg cccggggtac gggccggctg c 31

<210> SEQ ID NO 14
<211> LENGTH: 28
<212> TYPE: DNA
<213> ORGANISM: Artificial Sequence
<220> FEATURE:
<223> OTHER INFORMATION: Synthetic nucleotide containing the Xho I restriction enzyme recognition sequence

<400> SEQUENCE: 14
gggctcgagg gtccaggacc tggacatc 28

<210> SEQ ID NO 15
<211> LENGTH: 28
<212> TYPE: DNA
<213> ORGANISM: Artificial Sequence
<220> FEATURE:
<223> OTHER INFORMATION: Synthetic nucleotide containing the Xho I restriction enzyme recognition sequence

<400> SEQUENCE: 15
gggctcgagt cagcccgggg tacgggcc 28

<210> SEQ ID NO 16
<211> LENGTH: 153
<212> TYPE: PRT
<213> ORGANISM: Artificial Sequence
<220> FEATURE:
<223> OTHER INFORMATION: Synthtic peptide: Stx2eB-His-COMP
<220> FEATURE:
<221> NAME/KEY: DISULFID
<222> LOCATION: (3)..(56)
<223> OTHER INFORMATION: Intramolecular disulfide bond
<220> FEATURE:
<221> NAME/KEY: DISULFID
<222> LOCATION: (141)..(144)
<223> OTHER INFORMATION: Intermolecular disulfide bond from Cys141 of one molecule to Cys144 of another molecule

<400> SEQUENCE: 16

```
Met Asp Cys Ala Lys Gly Lys Ile Glu Phe Ser Lys Tyr Asn Glu Asp
1               5                   10                  15

Asn Thr Phe Thr Val Lys Val Ser Gly Arg Glu Tyr Trp Thr Asn Arg
            20                  25                  30

Trp Asn Leu Gln Pro Leu Leu Gln Ser Ala Gln Leu Thr Gly Met Thr
        35                  40                  45

Val Thr Ile Ile Ser Asn Thr Cys Ser Ser Gly Ser Gly Phe Ala Gln
    50                  55                  60
```

-continued

```
Val Lys Phe Asn Leu Glu Gly Pro Gly Pro Gly His His His His His
65                  70                  75                  80

His Glu Leu Gly Gly Gly Gly Ser Gly Gly Gly Gly Ser Gly Gly Gly
                85                  90                  95

Gly Ser Gly Gly Asp Leu Ala Pro Gln Met Leu Arg Glu Leu Gln Glu
            100                 105                 110

Thr Asn Ala Ala Leu Gln Asp Val Arg Glu Leu Leu Arg Gln Gln Val
        115                 120                 125

Lys Glu Ile Thr Phe Leu Lys Asn Thr Val Met Glu Cys Asp Ala Cys
    130                 135                 140

Gly Met Gln Pro Ala Arg Thr Pro Gly
145                 150


<210> SEQ ID NO 17
<211> LENGTH: 462
<212> TYPE: DNA
<213> ORGANISM: Artificial Sequence
<220> FEATURE:
<223> OTHER INFORMATION: Synthetic nucleotide: Stx2eB-His-COMP

<400> SEQUENCE: 17

atggattgcg cgaaaggcaa aattgaattt tcgaaatata atgaagataa cacctttacc      60

gtgaaagtga gcggtcgcga atattggacc aatcgttgga atctgcagcc gttactgcaa     120

tcggcccagc tgaccggcat gaccgttacc attatcagca acacctgcag ctcgggcagt     180

ggttttgcgc aggtgaaatt caatctcgag ggtccaggac ctggacatca tcaccatcac     240

catgaattgg gcggtggcgg tagcggcggt ggcggtagcg gcggtggcgg tagcggcggt     300

gatctggcgc cgcagatgct gcgcgaactg caggaaacca acgcggccct gcaagatgtg     360

cgtgaactgc tgcgccagca agtgaaagaa attacctttc tgaaaaatac cgttatggaa     420

tgcgatgcgt gtggcatgca gccggcccgt accccgggct ga                        462


<210> SEQ ID NO 18
<211> LENGTH: 231
<212> TYPE: PRT
<213> ORGANISM: Artificial Sequence
<220> FEATURE:
<223> OTHER INFORMATION: Synthetic peptide: Stx2eB-His-COMP-His-Z
<220> FEATURE:
<221> NAME/KEY: DISULFID
<222> LOCATION: (3)..(56)
<223> OTHER INFORMATION: Intramolecular disulfide bond
<220> FEATURE:
<221> NAME/KEY: DISULFID
<222> LOCATION: (141)..(144)
<223> OTHER INFORMATION: Intermolecular disulfide bond from Cys141 of
      one molecule to Cys144 of another molecule

<400> SEQUENCE: 18

Met Asp Cys Ala Lys Gly Lys Ile Glu Phe Ser Lys Tyr Asn Glu Asp
1               5                   10                  15

Asn Thr Phe Thr Val Lys Val Ser Gly Arg Glu Tyr Trp Thr Asn Arg
            20                  25                  30

Trp Asn Leu Gln Pro Leu Leu Gln Ser Ala Gln Leu Thr Gly Met Thr
        35                  40                  45

Val Thr Ile Ile Ser Asn Thr Cys Ser Ser Gly Ser Gly Phe Ala Gln
    50                  55                  60

Val Lys Phe Asn Leu Glu Gly Pro Gly Pro Gly His His His His His
65                  70                  75                  80
```

-continued

His Glu Leu Gly Gly Gly Gly Ser Gly Gly Gly Gly Ser Gly Gly Gly
85 90 95

Gly Ser Gly Gly Asp Leu Ala Pro Gln Met Leu Arg Glu Leu Gln Glu
100 105 110

Thr Asn Ala Ala Leu Gln Asp Val Arg Glu Leu Leu Arg Gln Gln Val
115 120 125

Lys Glu Ile Thr Phe Leu Lys Asn Thr Val Met Glu Cys Asp Ala Cys
130 135 140

Gly Leu Asp Gly Pro Gly Pro Gly Gly Gly Gly Ser His His His His
145 150 155 160

His His Gly Gly Gly Gly Ser Gly Pro Gly Pro Leu Asp Val Asp Asn
165 170 175

Lys Phe Asn Lys Glu Gln Gln Asn Ala Phe Tyr Glu Ile Leu His Leu
180 185 190

Pro Asn Leu Asn Glu Glu Gln Arg Asn Ala Phe Ile Gln Ser Leu Lys
195 200 205

Asp Asp Pro Ser Gln Ser Ala Asn Leu Leu Ala Glu Ala Lys Lys Leu
210 215 220

Asn Asp Ala Gln Ala Pro Lys
225 230

<210> SEQ ID NO 19
<211> LENGTH: 696
<212> TYPE: DNA
<213> ORGANISM: Artificial Sequence
<220> FEATURE:
<223> OTHER INFORMATION: Synthetic nucleotide: Stx2eB-His-COMP-His-Z

<400> SEQUENCE: 19
atggattgcg cgaaaggcaa aattgaattt tcgaaatata atgaagataa cacctttacc 60
gtgaaagtga gcggtcgcga atattggacc aatcgttgga atctgcagcc gttactgcaa 120
tcggcccagc tgaccggcat gaccgttacc attatcagca acacctgcag ctcgggcagt 180
ggttttgcgc aggtgaaatt caatctcgag ggtccaggac ctggacatca tcaccatcac 240
catgaattgg gcggtggcgg tagcggcggt ggcggtagcg gcggtggcgg tagcggcggt 300
gatctggcgc cgcagatgct gcgcgaactg caggaaacca acgcggccct gcaagatgtg 360
cgtgaactgc tgcgccagca agtgaaagaa attacctttc tgaaaaatac cgttatggaa 420
tgcgatgcgt gtggcctcga cggcccgggc ccgggcggtg gcggtagcca tcatcaccat 480
catcacggcg gtggcggtag cggcccgggc ccgctcgacg tggataacaa atttaataaa 540
gaacagcaga acgccttcta tgaaattctg catctgccga acctgaacga agaacagcgt 600
aacgccttta ttcagagcct gaaagatgat ccgagccaga gcgccaatct gctggcagaa 660
gccaaaaaac tgaacgatgc acaggccccg aaataa 696

<210> SEQ ID NO 20
<211> LENGTH: 87
<212> TYPE: PRT
<213> ORGANISM: Escherichia coli
<220> FEATURE:
<221> NAME/KEY: DISULFID
<222> LOCATION: (22)..(75)
<223> OTHER INFORMATION: Intramolecular disulfide bond

<400> SEQUENCE: 20

Met Lys Lys Met Phe Ile Ala Val Leu Phe Ala Leu Val Ser Val Asn
1 5 10 15

-continued

```
Ala Met Ala Ala Asp Cys Ala Lys Gly Lys Ile Glu Phe Ser Lys Tyr
            20                  25                  30

Asn Glu Asp Asn Thr Phe Thr Val Lys Val Ser Gly Arg Glu Tyr Trp
        35                  40                  45

Thr Asn Arg Trp Asn Leu Gln Pro Leu Leu Gln Ser Ala Gln Leu Thr
    50                  55                  60

Gly Met Thr Val Thr Ile Ile Ser Asn Thr Cys Ser Ser Gly Ser Gly
65                  70                  75                  80

Phe Ala Gln Val Lys Phe Asn
                85


<210> SEQ ID NO 21
<211> LENGTH: 207
<212> TYPE: DNA
<213> ORGANISM: Escherichia coli

<400> SEQUENCE: 21

gcggattgtg ctaaaggtaa aattgagttt tccaagtata atgaggataa tacctttact      60

gtgaaggtgt caggaagaga atactggacg aacagatgga atttgcagcc attgttacaa     120

agtgctcagc tgacagggat gactgtaaca atcatatcta atacctgcag ttcaggctca     180

ggctttgccc aggtgaagtt taactga                                         207


<210> SEQ ID NO 22
<211> LENGTH: 68
<212> TYPE: PRT
<213> ORGANISM: Escherichia coli
<220> FEATURE:
<221> NAME/KEY: DISULFID
<222> LOCATION: (3)..(56)
<223> OTHER INFORMATION: Intramolecular disulfide bond

<400> SEQUENCE: 22

Ala Asp Cys Ala Lys Gly Lys Ile Glu Phe Ser Lys Tyr Asn Glu Asp
1               5                   10                  15

Asn Thr Phe Thr Val Lys Val Ser Gly Arg Glu Tyr Trp Thr Asn Arg
            20                  25                  30

Trp Asn Leu Gln Pro Leu Leu Gln Ser Ala Gln Leu Thr Gly Met Thr
        35                  40                  45

Val Thr Ile Ile Ser Asn Thr Cys Ser Ser Gly Ser Gly Phe Ala Gln
    50                  55                  60

Val Lys Phe Asn
65


<210> SEQ ID NO 23
<211> LENGTH: 210
<212> TYPE: DNA
<213> ORGANISM: Artificial Sequence
<220> FEATURE:
<223> OTHER INFORMATION: Synthetic nucleotide modified for E. coli and
      yeast expression which does not contain secretion signals

<400> SEQUENCE: 23

atggattgcg cgaaaggcaa aattgaattt tcgaaatata atgaagataa cacctttacc      60

gtgaaagtga gcggtcgcga atattggacc aatcgttgga atctgcagcc gttactgcaa     120

tcggcccagc tgaccggcat gaccgttacc attatcagca acacctgcag ctcgggcagt     180

ggttttgcgc aggtgaaatt caatctcgag                                      210


<210> SEQ ID NO 24
```

-continued

<211> LENGTH: 70
<212> TYPE: PRT
<213> ORGANISM: Artificial Sequence
<220> FEATURE:
<223> OTHER INFORMATION: Synthetic peptide modified for E. coli and yeast expression which does not contain secretion signals
<220> FEATURE:
<221> NAME/KEY: DISULFID
<222> LOCATION: (3)..(56)
<223> OTHER INFORMATION: Intramolecular disulfide bond

<400> SEQUENCE: 24

Met Asp Cys Ala Lys Gly Lys Ile Glu Phe Ser Lys Tyr Asn Glu Asp
1               5                   10                  15

Asn Thr Phe Thr Val Lys Val Ser Gly Arg Glu Tyr Trp Thr Asn Arg
            20                  25                  30

Trp Asn Leu Gln Pro Leu Leu Gln Ser Ala Gln Leu Thr Gly Met Thr
        35                  40                  45

Val Thr Ile Ile Ser Asn Thr Cys Ser Ser Gly Ser Gly Phe Ala Gln
    50                  55                  60

Val Lys Phe Asn Leu Glu
65                  70

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide: (G4S)3 linker

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 165
<212> TYPE: DNA
<213> ORGANISM: Artificial Sequence
<220> FEATURE:
<223> OTHER INFORMATION: Synthetic nucleotide encoding a polypeptide having the coiled-coil forming unit of COMP

<400> SEQUENCE: 26
ggtggagacc tagccccaca gatgcttcga gaactccagg agactaatgc ggcgctgcaa      60
gacgtgagag agctcttgcg acagcaggtc aaggagatca ccttcctgaa gaatacggtg     120
atggaatgtg acgcttgcgg aatgcagccc gcacgcaccc ccggt                     165

<210> SEQ ID NO 27
<211> LENGTH: 55
<212> TYPE: PRT
<213> ORGANISM: Artificial Sequence
<220> FEATURE:
<223> OTHER INFORMATION: Synthetic polypeptide having the coiled-coil forming unit of COMP
<220> FEATURE:
<221> NAME/KEY: DISULFID
<222> LOCATION: (43)..(46)
<223> OTHER INFORMATION: Intermolecular disulfide bond from Cys43 of one molecule to Cys46 of another molecule

<400> SEQUENCE: 27

Gly Gly Asp Leu Ala Pro Gln Met Leu Arg Glu Leu Gln Glu Thr Asn
1               5                   10                  15

Ala Ala Leu Gln Asp Val Arg Glu Leu Leu Arg Gln Gln Val Lys Glu
            20                  25                  30

-continued

Ile Thr Phe Leu Lys Asn Thr Val Met Glu Cys Asp Ala Cys Gly Met
35 40 45

Gln Pro Ala Arg Thr Pro Gly
50 55

<210> SEQ ID NO 28
<211> LENGTH: 55
<212> TYPE: PRT
<213> ORGANISM: Artificial Sequence
<220> FEATURE:
<223> OTHER INFORMATION: Synthetic peptide modified for E. coli and yeast expression
<220> FEATURE:
<221> NAME/KEY: DISULFID
<222> LOCATION: (43)..(46)
<223> OTHER INFORMATION: Intermolecular disulfide bond from Cys43 of one molecule to Cys46 of another molecule

<400> SEQUENCE: 28

Gly Gly Asp Leu Ala Pro Gln Met Leu Arg Glu Leu Gln Glu Thr Asn
1 5 10 15

Ala Ala Leu Gln Asp Val Arg Glu Leu Leu Arg Gln Gln Val Lys Glu
20 25 30

Ile Thr Phe Leu Lys Asn Thr Val Met Glu Cys Asp Ala Cys Gly Met
35 40 45

Gln Pro Ala Arg Thr Pro Gly
50 55

<210> SEQ ID NO 29
<211> LENGTH: 70
<212> TYPE: PRT
<213> ORGANISM: Artificial Sequence
<220> FEATURE:
<223> OTHER INFORMATION: Synthetic peptide: Encoding (G4S)3 linker and COMP
<220> FEATURE:
<221> NAME/KEY: DISULFID
<222> LOCATION: (58)..(61)
<223> OTHER INFORMATION: Intermolecular disulfide bond from Cys58 of one molecule to Cys61 of another molecule

<400> SEQUENCE: 29

Gly Gly Gly Gly Ser Gly Gly Gly Gly Ser Gly Gly Gly Gly Ser Gly
1 5 10 15

Gly Asp Leu Ala Pro Gln Met Leu Arg Glu Leu Gln Glu Thr Asn Ala
20 25 30

Ala Leu Gln Asp Val Arg Glu Leu Leu Arg Gln Gln Val Lys Glu Ile
35 40 45

Thr Phe Leu Lys Asn Thr Val Met Glu Cys Asp Ala Cys Gly Met Gln
50 55 60

Pro Ala Arg Thr Pro Gly
65 70

<210> SEQ ID NO 30
<211> LENGTH: 129
<212> TYPE: DNA
<213> ORGANISM: Gallus gallus

<400> SEQUENCE: 30
gaggaagatc catgcgaatg taaatctata gtgaagttcc agacaaaagt tgaagaactc 60
atcaatacac tgcagcagaa attggaagct gtggcaaaaa ggattgaagc cctggagaat 120
aagatcatc 129

<210> SEQ ID NO 31
<211> LENGTH: 129
<212> TYPE: DNA
<213> ORGANISM: Artificial Sequence
<220> FEATURE:
<223> OTHER INFORMATION: Synthetic nucleotide modified for E.coli and
yeast expression

<400> SEQUENCE: 31
gaagaagatc cgtgcgaatg taaatccatt gtgaaatttc agaccaaagt tgaagaactg 60
atcaacacgc tgcaacaaaa actggaagcg gtggcgaaac gcattgaagc actggaaaac 120
aaaatcatc 129

<210> SEQ ID NO 32
<211> LENGTH: 43
<212> TYPE: PRT
<213> ORGANISM: Gallus gallus
<220> FEATURE:
<221> NAME/KEY: DISULFID
<222> LOCATION: (5)..(7)
<223> OTHER INFORMATION: Intermolecular disulfide bond from Cys5 of one
molecule to Cys7 of another molecule

<400> SEQUENCE: 32

Glu Glu Asp Pro Cys Glu Cys Lys Ser Ile Val Lys Phe Gln Thr Lys
1 5 10 15

Val Glu Glu Leu Ile Asn Thr Leu Gln Gln Lys Leu Glu Ala Val Ala
20 25 30

Lys Arg Ile Glu Ala Leu Glu Asn Lys Ile Ile
35 40

<210> SEQ ID NO 33
<211> LENGTH: 43
<212> TYPE: PRT
<213> ORGANISM: Artificial Sequence
<220> FEATURE:
<223> OTHER INFORMATION: Synthetic peptide modified for E.coli and yeast
expression
<220> FEATURE:
<221> NAME/KEY: DISULFID
<222> LOCATION: (5)..(7)
<223> OTHER INFORMATION: Intermolecular disulfide bond from Cys5 of one
molecule to Cys7 of another molecule

<400> SEQUENCE: 33

Glu Glu Asp Pro Cys Glu Cys Lys Ser Ile Val Lys Phe Gln Thr Lys
1 5 10 15

Val Glu Glu Leu Ile Asn Thr Leu Gln Gln Lys Leu Glu Ala Val Ala
20 25 30

Lys Arg Ile Glu Ala Leu Glu Asn Lys Ile Ile
35 40

<210> SEQ ID NO 34
<211> LENGTH: 426
<212> TYPE: DNA
<213> ORGANISM: Artificial Sequence
<220> FEATURE:
<223> OTHER INFORMATION: Synthetic nucleotide: Stx2eB-His-CMP

<400> SEQUENCE: 34
atggactgtg cgaaaggcaa aatcgaattt agcaaataca atgaagataa tacgtttacg 60
gtgaaagtgt cgggtcgtga atactggacc aaccgttgga atctgcagcc gctgctgcag 120

-continued tctgcgcaac tgaccggtat gaccgtcacg attatctcga acacgtgcag ctctggcagc 180
ggttttgccc aagttaaatt caatctggaa ggcccgggtc cgggccatca ccatcaccat 240
cacgaactgg gcggtggcgg tagtggcggt ggcggttccg gcggtggcgg ttcagaagaa 300
gatccgtgcg aatgtaaatc cattgtgaaa tttcagacca aagttgaaga actgatcaac 360
acgctgcaac aaaaactgga agcggtggcg aaacgcattg aagcactgga aaacaaaatc 420
atctaa 426

<210> SEQ ID NO 35
<211> LENGTH: 141
<212> TYPE: PRT
<213> ORGANISM: Artificial Sequence
<220> FEATURE:
<223> OTHER INFORMATION: Synthetic peptide: Stx2eB-His-CMP
<220> FEATURE:
<221> NAME/KEY: DISULFID
<222> LOCATION: (3)..(56)
<223> OTHER INFORMATION: Intramolecular disulfide bond
<220> FEATURE:
<221> NAME/KEY: DISULFID
<222> LOCATION: (103)..(105)
<223> OTHER INFORMATION: Intermolecular disulfide bond from Cys103 of one molecule to Cys105 of another molecule

<400> SEQUENCE: 35

Met Asp Cys Ala Lys Gly Lys Ile Glu Phe Ser Lys Tyr Asn Glu Asp
1 5 10 15

Asn Thr Phe Thr Val Lys Val Ser Gly Arg Glu Tyr Trp Thr Asn Arg
20 25 30

Trp Asn Leu Gln Pro Leu Leu Gln Ser Ala Gln Leu Thr Gly Met Thr
35 40 45

Val Thr Ile Ile Ser Asn Thr Cys Ser Ser Gly Ser Gly Phe Ala Gln
50 55 60

Val Lys Phe Asn Leu Glu Gly Pro Gly Pro Gly His His His His His
65 70 75 80

His Glu Leu Gly Gly Gly Gly Ser Gly Gly Gly Gly Ser Gly Gly Gly
85 90 95

Gly Ser Glu Glu Asp Pro Cys Glu Cys Lys Ser Ile Val Lys Phe Gln
100 105 110

Thr Lys Val Glu Glu Leu Ile Asn Thr Leu Gln Gln Lys Leu Glu Ala
115 120 125

Val Ala Lys Arg Ile Glu Ala Leu Glu Asn Lys Ile Ile
130 135 140

<210> SEQ ID NO 36
<211> LENGTH: 473
<212> TYPE: DNA
<213> ORGANISM: Artificial Sequence
<220> FEATURE:
<223> OTHER INFORMATION: Synthetic nucleotide: Stx2eB-His-CMP

<400> SEQUENCE: 36
agaaggagat ataccatgga ctgtgcgaaa ggcaaaatcg aatttagcaa atacaatgaa 60
gataatacgt ttacggtgaa agtgtcgggt cgtgaatact ggaccaaccg ttggaatctg 120
cagccgctgc tgcagtctgc gcaactgacc ggtatgaccg tcacgattat ctcgaacacg 180
tgcagctctg gcagcggttt tgcccaagtt aaattcaatc tggaaggccc gggtccgggc 240
catcaccatc accatcacga actgggcggt ggcggtagtg gcggtggcgg ttccggcggt 300
ggcggttcag aagaagatcc gtgcgaatgt aaatccattg tgaaatttca gaccaaagtt 360

-continued

```
gaagaactga tcaacacgct gcaacaaaaa ctggaagcgg tggcgaaacg cattgaagca    420

ctggaaaaca aaatcatcta actcgagcac caccaccacc accactgaga tcc           473
```

VACCINE FOR PREVENTING PORCINE EDEMA DISEASE

TECHNICAL FIELD

The present invention relates to a vaccine for preventing porcine edema disease. More specifically, the vaccine contains a recombinant protein in which a polypeptide having a coiled-coil forming unit and a B subunit of Stx2e (Stx2eB), which is a toxin causing porcine edema disease, are fused and/or a multimer thereof as an active ingredient. By vaccinating pigs with the fusion protein and/or the multimer, potent toxin-neutralizing antibodies are induced, and the vaccine can prevent the onset of edema disease.

BACKGROUND ART

Porcine edema disease often breaks out among young pigs of 4 to 12 weeks old, causes eyelid edema, neurological symptoms and the like and mostly results in death within 24 hours of the onset (NPL 1, Proc. Jpn. Pig Vet. Soc. 2006, 48, 7-13). Its fatality rate is as high as 50 to 90%, and the economic loss is enormous because the productivity decreases due to the recurrence, incomplete development and the like. This disease is caused by Shiga toxin Stx2e produced by Shiga toxin producing *Escherichia coli* (Shiga toxin producing *E. coli*, STEC) which is adhered to the intestinal tract. Stx2e is an $AB_5$-type toxin protein containing an A subunit (Stx2eA) having rRNA N-glycosidase activity and a B subunit pentamer (Stx2eB) having a capability of binding to a receptor (globotetraosyl ceramide (Gb4)). It is known that Stx2e which has been taken from the intestinal tract and brought to the surface of a cell such as a vascular endothelial cell by the B subunit sends the A subunit into the cytoplasm of the target cell and inhibits the protein synthesis by the ribosome, thereby inducing the symptoms of edema disease. In Japan, no vaccine for preventing porcine edema disease is commercially available, and although antibiotics are used, the administration after the onset is usually too late. Furthermore, drug-resistant bacteria have been reported, and development of effective preventive method and therapeutic method is desired.

Under these circumstances, methods for effectively preventing porcine edema disease have been investigated. For example, a case of immunization with an Stx2e toxoid has shown an effect of defending against experimental infection (NPL 2, Vet. Microbiol. 1991, 29, 309-318). However, in another report, the onset of edema disease has been observed in some pigs after immunization with a toxoid because detoxification is difficult (NPL 3, Infect. Immun. 1992, 60, 485-90). Moreover, in another example, it is reported that the induction of neutralizing antibodies was confirmed when pigs were immunized with recombinant Stx2e which was detoxified by modifying a part of the amino acid sequence of Stx2eA (NPL 3, Infect. Immun. 1992, 60, 485-90). However, the production of detoxified Stx2e by recombinant *E. coli* is extremely low, and there are still problems for the practical use.

CITATION LIST

Patent Literature

PTL 1: JP-A-2008-50344

Non Patent Literature

NPL 1: Proc. Jpn. Pig Vet. Soc. 2006, 48, 7-13
NPL 2: Vet. Microbiol. 1991, 29, 309-318

NPL 3: Infect. Immun. 1992, 60, 485-90
NPL 4: Adv. Protein Chem. 2005, 70, 37-78
NPL 5: Infect. Immun. 2005, 7, 5654-65
NPL 6: Infect. Immun. 2011, 79(10), 4260-4275

SUMMARY OF INVENTION

Technical Problem

An aim that the invention is to achieve is to provide farms where the onset of porcine edema disease is anticipated with a vaccine which can effectively prevent porcine edema disease.

Solution to Problem

The inventors of the invention have studied intensively to achieve the aim and as a result found that potent toxin-neutralizing antibodies are induced by vaccinating pigs with a fusion protein of a polypeptide having a coiled-coil forming unit and Stx2eB as a vaccine. Thus, the inventors have completed the invention.

That is, the invention is as follows.

[1] A fusion protein in which a polypeptide having a coiled-coil forming unit and a B subunit of Shiga toxin Stx2e (Stx2eB) are joined.

[2] The fusion protein described in [1] having a linker sequence and/or a tag sequence between the polypeptide and the Stx2eB.

[3] The fusion protein described in [1] or [2], wherein the coiled-coil forming unit is derived from a natural multimer-forming protein.

[4] The fusion protein described in [3], wherein the natural multimer-forming protein is selected from the group consisting of cartilage oligomeric matrix protein (COMP), cartilage matrix protein (CMP), tetrabrachion (TB) and GCN4.

[5] The fusion protein described in [4], wherein the natural multimer-forming protein is COMP or CMP.

[6] The fusion protein described in [5], wherein the natural multimer-forming protein is COMP.

[7] The fusion protein described in [6] which is a polypeptide comprising the amino acid sequence represented by SEQ ID NO:27 or SEQ ID NO:28 or a polypeptide comprising the amino acid sequence represented by SEQ ID NO:27 or SEQ ID NO:28 with deletion, substitution or insertion of one or several amino acid residues.

[8] The fusion protein described in [5], wherein the natural multimer-forming protein is CMP.

[9] The fusion protein described in [8] which is a polypeptide comprising the amino acid sequence represented by SEQ ID NO:32 or SEQ ID NO:33 or a polypeptide comprising the amino acid sequence represented by SEQ ID NO:32 or SEQ ID NO:33 with deletion, substitution or insertion of one or several amino acid residues.

[10] The fusion protein described in any one of [1] to [9], wherein the Stx2eB is a polypeptide comprising the amino acid sequence represented by SEQ ID NO:20, SEQ ID NO:22 or SEQ ID NO:24 or a polypeptide comprising the amino acid sequence represented by SEQ ID NO:20, SEQ ID NO:22 or SEQ ID NO:24 with deletion, substitution or insertion of one or several amino acid residues.

[11] A fusion protein multimer in which the fusion protein described in any one of [1] to [10] is multimerized.

[12] A nucleic acid fragment comprising a DNA sequence encoding the fusion protein described in any one of [1] to [10].

[13] A recombinant expression vector containing the nucleic acid fragment described in [12].

[14] A transformant containing the nucleic acid fragment described in [12].

[15] A transformant containing the recombinant expression vector described in [13].

[16] An antibody capable of binding to the fusion protein described in any one of [1] to [10].

[17] An antibody capable of binding to the fusion protein multimer described in [11].

[18] A vaccine against porcine edema disease containing the fusion protein described in any one of [1] to [10] as an active ingredient.

[19] A vaccine against porcine edema disease containing the fusion protein multimer described in [11] as an active ingredient.

[20] An agent for treating porcine edema disease containing the antibody described in [16] or [17] as an active ingredient.

[21] A DNA vaccine against porcine edema disease containing the nucleic acid fragment described in [12] as an active ingredient.

[22] A DNA vaccine against porcine edema disease containing the recombinant expression vector described in [13] as an active ingredient.

[23] A kit for measuring the amount of antibodies to the Stx2eB in a sample, containing the fusion protein described in any one of [1] to [10].

[24] A kit for measuring the amount of antibodies to the Stx2eB in a sample, containing the fusion protein multimer described in [11].

[25] A kit for measuring the Stx2eB content in a sample, containing the antibody described in [16] or [17].

[26] A method for producing a fusion protein multimer, containing a process of expressing a fusion protein in which a polypeptide having a coiled-coil forming unit and a B subunit of Shiga toxin Stx2e (Stx2eB) are joined in a host and then refolding the fusion protein.

[27] The production method described in [26], wherein the fusion protein has a spacer between the polypeptide and the Stx2eB.

[28] The production method described in [26] or [27], wherein the polypeptide has a coiled-coil forming unit derived from a natural multimer-forming protein which is selected from the group consisting of cartilage oligomeric matrix protein (COMP), cartilage matrix protein (CMP), tetrabrachion (TB) and GCN4.

[29] The production method described in [28], wherein the polypeptide has a coiled-coil forming unit derived from COMP or CMP.

[30] The production method described in [29], wherein the polypeptide has a coiled-coil forming unit derived from COMP.

[31] The production method described in [30], wherein the polypeptide is a polypeptide comprising the amino acid sequence represented by SEQ ID NO:27 or SEQ ID NO:28 or a polypeptide comprising the amino acid sequence represented by SEQ ID NO:27 or SEQ ID NO:28 with deletion, substitution or insertion of one or several amino acid residues.

[32] The production method described in [29], wherein the polypeptide has a coiled-coil forming unit derived from CMP.

[33] The production method described in [32], wherein the polypeptide is a polypeptide comprising the amino acid sequence represented by SEQ ID NO:32 or SEQ ID NO:33 or a polypeptide comprising the amino acid sequence represented by SEQ ID NO:32 or SEQ ID NO:33 with deletion, substitution or insertion of one or several amino acid residues.

[34] The production method described in any one of [26] to [33], wherein the Stx2eB is a polypeptide comprising the amino acid sequence represented by SEQ ID NO:20, SEQ ID NO:22 or SEQ ID NO:24 or a polypeptide comprising the amino acid sequence represented by SEQ ID NO:20, SEQ ID NO:22 or SEQ ID NO:24 with deletion, substitution or insertion of one or several amino acid residues.

[35] A method for preventing porcine edema disease by administering the fusion protein described in any one of [1] to [10] to a pig.

[36] A method for preventing porcine edema disease by administering the fusion protein multimer described in [11] to a pig.

[37] A method for treating porcine edema disease by administering the antibody described in [16] or [17] to a pig.

[38] A method for preventing porcine edema disease by administering the nucleic acid fragment described in [12] to a pig.

[39] A method for preventing porcine edema disease by administering the recombinant expression vector described in [13] to a pig.

Advantageous Effects of Invention

When pigs are inoculated with a vaccine containing as an active ingredient a fusion protein in which a polypeptide having a coiled-coil forming unit and Stx2eB are joined, it is possible to induce potent toxin-neutralizing antibodies and prevent the onset of porcine edema disease.

BRIEF DESCRIPTION OF DRAWINGS

FIG. 1 A schematic diagram of Stx2eB-His.

FIG. 2 A schematic diagram of Stx2eB-His-COMP.

FIG. 3 A figure showing the formation of multimers of Stx2eB-His-COMP observed.

FIG. 4 A schematic diagram of Stx2eB-His-COMP-Z.

DESCRIPTION OF EMBODIMENTS (1) Fusion Protein

Figure 5:
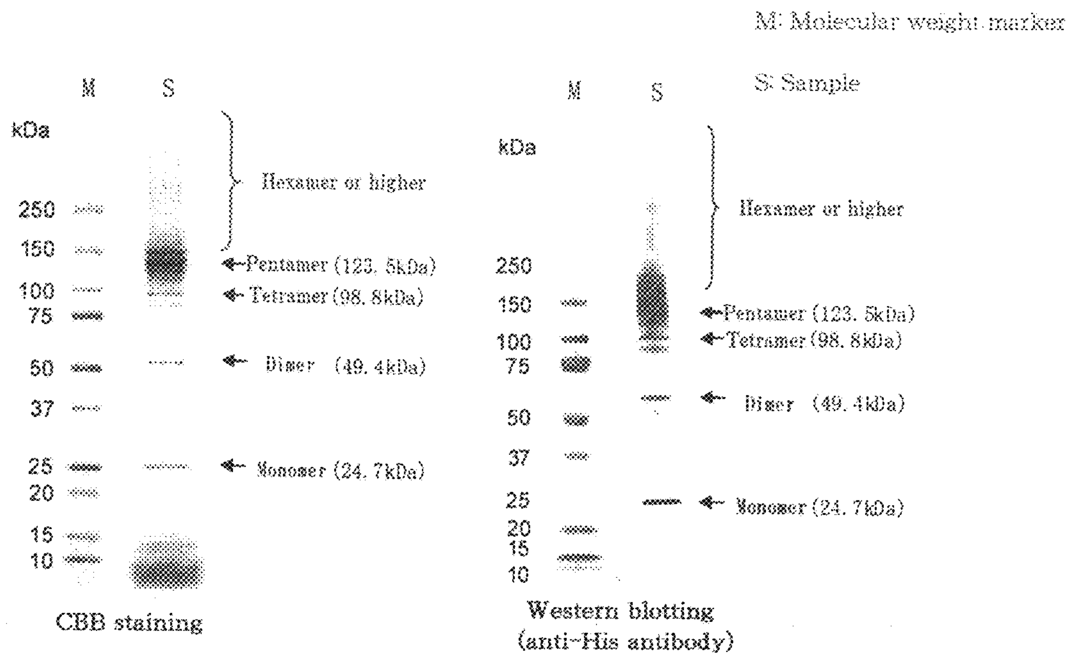
FIG. 5 A figure showing the formation of multimers of Stx2eB-His-COMP-Z observed.

The invention includes a fusion protein in which a polypeptide having a coiled-coil forming unit and a B subunit of Shiga toxin Stx2e (Stx2eB) are joined.

Examples of Stx2eB constituting the fusion protein of the invention are precursor Stx2eB containing a secretory signal (for example, SEQ ID NO:1 and SEQ ID NO:20), mature Stx2eB without a secretory signal (for example, SEQ ID NO:21 and SEQ ID NO:22) and Stx2eB obtained by optimizing the codons of mature Stx2eB for expression in *E. coli* and yeast (for example, SEQ ID NO:23 and SEQ ID NO:24).

As the DNA sequence encoding Stx2eB (the DNA sequence of Stx2eB), in addition to the DNA sequences of SEQ ID NO:1, SEQ ID NO:21 and SEQ ID NO:23, these DNA sequences to which an appropriate cleavage site for a restriction enzyme is added and these DNA sequences with deletion, substitution or insertion of one or several nucleotides are included. Moreover, DNA sequences each having a homology of 80% or more, preferably 90% or more, more preferably 95% or more, to these DNA sequences are also included.

Stx2eB includes polypeptides comprising the amino acid sequences represented by SEQ ID NO:20, SEQ ID NO:22 and SEQ ID NO:24 and polypeptides comprising these amino acid sequences with deletion, substitution or insertion of one or several amino acid residues. Moreover, polypeptides comprising amino acid sequences each having a homology of 80% or more, preferably 90% or more, more preferably 95% or more, to these amino acid sequences are also included.

On the other hand, the polypeptide having a coiled-coil forming unit which is joined with Stx2eB to constitute the fusion protein of the invention is not particularly limited as long as it is capable of forming a coiled-coil structure, but a polypeptide having a coiled-coil forming unit derived from a natural protein which forms a multimer (multimer-forming protein) is preferable. For instance, the multimer-forming protein described in NPL 4 (Adv Protein Chem. 2005, 70, 37-78) is an example, and those having a coiled-coil forming unit derived from a multimer-forming protein such as COMP (cartilage oligomeric matrix protein, pentamer), tetrabrachion (TB, tetramer) derived from *Staphylothermus marinus*, GCN4 (trimer) and cartilage matrix protein (CMP, trimer) derived from a chicken are mentioned. Among them, a polypeptide having a coiled-coil forming unit derived from a protein which forms a pentamer (such as COMP) or a trimer (such as CMP) is preferable, and a polypeptide having a coiled-coil forming unit derived from a protein which forms a pentamer such as COMP is particularly preferable, because the fusion protein of such a polypeptide and Stx2eB is a soluble protein which is less cohesive and is excellent in the effect of inducing toxin-neutralizing antibodies.

As the DNA sequence encoding the polypeptide having the coiled-coil forming unit of COMP (the DNA sequence of the coiled-coil forming unit), in addition to the DNA sequence of SEQ ID NO:26, sequences with codons optimized for expression in *E. coli* and yeast (for example, SEQ ID NO:10), these DNA sequences to which an appropriate cleavage site for a restriction enzyme is added and these DNA sequences with deletion, substitution or insertion of one or several nucleotides are included. Moreover, DNA sequences each having a homology of 80% or more, preferably 90% or more, more preferably 95% or more, to these DNA sequences are also included.

Furthermore, the polypeptide having the coiled-coil forming unit of COMP includes polypeptides comprising the amino acid sequences represented by SEQ ID NO:27 and sequences with codons optimized for expression in *E. coli* and yeast (for example, SEQ ID NO:28) and polypeptides comprising these amino acid sequences with deletion, substitution or insertion of one or several amino acid residues. Moreover, polypeptides comprising amino acid sequences each having a homology of 80% or more, preferably 90% or more, more preferably 95% or more, to these amino acid sequences are also included.

As the DNA sequence encoding the polypeptide having the coiled-coil forming unit of CMP (the DNA sequence of the coiled-coil structure), in addition to the DNA sequence of SEQ ID NO:30, sequences with codons optimized for expression in *E. coli* and yeast (for example, SEQ ID NO:31), these DNA sequences to which an appropriate cleavage site for a restriction enzyme is added and these DNA sequences with deletion, substitution or insertion of one or several nucleotides are included. Moreover, DNA sequences each having a homology of 80% or more, preferably 90% or more, more preferably 95% or more, to these DNA sequences are also included.

Furthermore, the polypeptide having the coiled-coil forming unit of CMP includes polypeptides comprising the amino acid sequences represented by SEQ ID NO:32 and sequences with codons optimized for expression in *E. coli* and yeast (for example, SEQ ID NO:33) and polypeptides comprising these amino acid sequences with deletion, substitution or insertion of one or several amino acid residues. Moreover, polypeptides comprising amino acid sequences each having a homology of 80% or more, preferably 90% or more, more preferably 95% or more, to these amino acid sequences are also included.

In the fusion protein of the invention, the peptide having the coiled-coil forming unit and Stx2eB may be adjacent and joined to each other, or a spacer such as a linker sequence and a tag sequence may be inserted between the peptide and Stx2eB for the purpose of reducing the intermolecular interactions or the like. The linker sequence is not particularly limited, but for example, a sequence having a combination of GPGP or GGGGS ($G_4S$) can be used. Moreover, a sequence having one to four ($G_4S$) ($(G_4S)_1$ to $(G_4S)_4$) can also be used as the linker sequence, and $(GP)_2$ may be further combined. Examples of the tag sequence are glutathione-S-transferase (GST), maltose-binding protein (MBP) and Hisx6 ($H_6$). A preferable example of the combination of the tag sequence and the linker sequence is $(GP)_2GH_6(G_4S)_3$. Moreover, it is possible to replace the ($G_4S$) partial sequence in the sequence with a repetitive sequence ($(G_4S)_{1\ to\ 3}$). Furthermore, $GPGPH_6GPGP$ and $G_4SH_6G_4S$ sequences can also be used.

An example of the fusion protein of the invention is a fusion protein of the polypeptide having the coiled-coil forming unit of COMP and Stx2eB with codons optimized for expression in *E. coli* and yeast, wherein a tag sequence ($H_6$) and a linker sequence ($(G_4S)_3$) are inserted between the polypeptide and Stx2eB (for example, SEQ ID NO:17 or SEQ ID NO:16). The fusion protein of the invention includes not only the protein having the amino acid sequence of SEQ ID NO:16 but also a polypeptide comprising the amino acid sequence with deletion, substitution or insertion of one or several amino acid residues. Moreover, polypeptides comprising amino acid sequences each having a homology of 80% or more, preferably 90% or more, more preferably 95% or more, to these amino acid sequences are also included.

In addition, another example of the fusion protein of the invention is a fusion protein of the polypeptide having the coiled-coil forming unit of CMP and Stx2eB with codons optimized for expression in *E. coli* and yeast, wherein a tag sequence ($H_6$) and a linker sequence ($(G_4S)_3$) are inserted between the polypeptide and Stx2eB (for example, SEQ ID NO:34 or SEQ ID NO:35). The fusion protein of the invention includes not only the protein having the amino acid sequence of SEQ ID NO:35 but also a polypeptide comprising the amino acid sequence with deletion, substitution or insertion of one or several amino acid residues. Moreover, polypeptides comprising amino acid sequences each having a homology of 80% or more, preferably 90% or more, more preferably 95% or more, to these amino acid sequences are also included.

When the polypeptide having the coiled-coil forming unit and Stx2eB are joined, the polypeptide and Stx2eB may be joined by genetic engineering and then expressed. For example, in one method, an expression vector is prepared in such a way that the DNA sequence of the coiled-coil forming unit and the DNA sequence of Stx2eB are adjacent to each other and then introduced into an appropriate host, and the fusion protein is expressed. The DNA sequence of the coiled-coil forming unit may be either at the 5' end or the 3' end of the DNA sequence of Stx2eB. Preferably, the DNA sequence of the coiled-coil forming unit is at the 3' end. When the expression vector is prepared, a DNA sequence of the linker sequence and/or tag sequence may be inserted between the DNA sequence of the coiled-coil forming unit and the DNA sequence of Stx2eB or attached to the 5' end or the 3' end of the DNA sequence. For example, in one method, an expression vector is prepared in such a way that the DNA sequence of Stx2eB, the DNA sequence of the tag sequence and/or linker sequence and the DNA sequence of the coiled-coil forming unit are aligned in this order from the 5' end.

The DNA sequence above can be obtained by chemical synthesis and used as a template for a known gene amplification method to amplify the DNA fragment, and a recombinant expression vector can be prepared by inserting the DNA fragment into an expression vector using a restriction enzyme. The oligonucleotides used for the gene amplification are designed to hybridize with the 5' end or 3' end of the template DNA sequence and preferably contain a cleavage site for a restriction enzyme. The template DNA can be amplified by a known gene amplification method using the oligonucleotides, the template DNA, a DNA polymerase and the like. By treating the amplified DNA sequence and an expression vector with a restriction enzyme and then joining them with an appropriate DNA ligase, a recombinant expression vector containing the target DNA sequence can be constructed. Such a recombinant expression vector is also included in the invention.

The expression vector is a plasmid vector, a phage vector, a viral vector, an artificial chromosome vector or the like, and a plasmid vector is preferable because of the easiness of handling and the cost. For example, when the host is *E. coli*, the expression vector is pFN6A (HQ) Flexi Vector (Promega), pFN7A (HQ) Flexi Vector (Promega), pFN2A (GST) Flexi Vector (Promega), pET-22b (MERCK), pET-21d (MERCK), pCold vector (Takara Bio Inc.) or the like, while when the host is a mammal, the expression vector is pF4A CMV Flexi Vector (Promega), pF5A CMV-neo Flexi Vector (Promega), pF9A CMV hRluc-neo Flexi Vector (Promega) or pCI-neo Mammalian Expression Vector (Promega). The expression vector may contain a replication origin, a regulatory sequence which plays a role of regulating the gene expression such as a promoter sequence and an enhancer sequence and the sequence of a selection marker.

As examples of the promoter sequence, bacterial promoters are *E. coli* lad and lacZ promoters, T3 and T7 promoters, gpt promoter, lambda PR, PL promoter, tac promoter and trp and trc promoters. Known eukaryotic promoters which are appropriate in this regard are cytomegalovirus ("CMV") immediate-early promoter, HSV thymidine kinase promoter, SV40 early and late promoters, retrovirus LTR promoter, Rous sarcoma virus ("RoSV") promoter, for example, and metallothionein promoters such as metallothionein-I promoter.

When the fusion protein is expressed using a higher eukaryotic cell as a host, the transcriptional activity can be enhanced by inserting an enhancer sequence into the expression vector. The enhancer sequence acts to enhance the transcriptional activity of the promoter in a certain host cell. Examples of the enhancer include SV40 enhancer, cytomegalovirus early promoter enhancer, polyoma enhancer downstream of the replication origin, β-actin enhancer and adenovirus enhancer.

Examples of the selection marker are an ampicillin-resistant gene of *E. coli*, the trp1 gene of *Saccharomyces serevisiae* and a neomycin-resistant gene of a mammalian cell.

The invention includes a nucleic acid fragment which encodes the fusion protein of the invention and contains the DNA sequence of the coiled-coil forming unit and the DNA sequence of Stx2eB. The nucleic acid fragment of the invention includes a nucleic acid fragment containing the DNA sequence of the coiled-coil forming unit and the DNA sequence of Stx2eB which are aligned adjacent to each other or a nucleic acid fragment containing the DNA sequence of the tag sequence and/or linker sequence between the DNA sequence of the coiled-coil forming unit and the DNA sequence of Stx2eB. For example, the nucleic acid fragments of SEQ ID NOs:17 and 34 are included.

The whole sequence of the nucleic acid fragment of the invention can be obtained by chemical synthesis. In addition, a part of the nucleic acid fragment and the remaining part of the nucleic acid fragment may be first obtained by chemical synthesis and then joined by a known gene recombination technique. For example, after chemically synthesizing the DNA sequences of Stx2eB and the coiled-coil forming unit, the DNA fragments are amplified by a known gene amplification method and inserted into separate cloning vectors. The DNA sequence of Stx2eB and the DNA sequence of the coiled-coil forming unit are cut out from the respective cloning vectors using a restriction enzyme and then inserted into an expression vector which has also been treated with a restriction enzyme, thereby preparing a recombinant expression vector. The insertion process should be designed so that the fragments are aligned adjacent to each other. Then, by cutting out the nucleic acid fragment from the recombinant expression vector using a restriction enzyme or the like, the nucleic acid fragment in which the DNA sequences of the coiled-coil forming unit and Stx2eB are joined can be obtained. When the nucleic acid fragment is prepared by the above method, the DNA sequence of the tag sequence or the linker sequence may be inserted between the DNA sequences of the coiled-coil forming unit and Stx2eB to prepare the expression vector and prepare the nucleic acid fragment.

By transfecting a host with the expression vector prepared above, a transformant containing the expression vector can be obtained. Such a transformant is also included in the invention. The host is a known host such as *E. coli*, yeast, a mammalian cell line, an insect cell and a plant. Examples of *E. coli* are BL21 strain and DH5α. Yeast is *Pichia pastoris* or *Saccharomyces cerevisiae*, and the mammalian cell is CHO cell, HEK293 cell, COS-1/-7 cell or the like.

The host can be transfected with the expression vector by a known method according to the host, and examples are a method using calcium phosphate, electroporation and lipofection. After the transfection, the transformant, which is the host cell which has taken up the expression vector, can be selected by culturing in a culture medium containing a selection marker.

By proliferating the transformant prepared above under a preferable condition and then inducing the selected promoter under a specific condition (pH, temperature or addition of a compound), the fusion protein can be produced. The fusion protein expressed is accumulated in the cell or secreted from the cell.

When expressed in *E. coli* as the host, the fusion protein may be expressed in the inclusion body fraction. Examples of the method for recovering the inclusion bodies from *E.*

*coli* are ultrasonic fragmentation, high pressure homogenization and a method using BugBuster (Merck KGaA).

The fusion protein of the invention thus obtained can be used as a monomer, but it is preferable to form a multimer because potent toxin-neutralizing antibodies can be induced. For example, the fusion protein multimer is a dimer, a trimer, a tetramer, a pentamer or a higher multimer, and a mixture of the multimers is also included. In order to form such a fusion protein multimer, for example, the inclusion bodies are recovered from *E. coli* as describe above, the fusion protein is solubilized, and then the solubilized solution is subjected to refolding treatment. Examples of the method for solubilizing the fusion protein from the inclusion bodies are a method for adding guanidine hydrochloride or a urea solution to the inclusion bodies, Inclusion Body Solubilization Reagent (Funakoshi) and Proteospin Inclusion Body Isolation Kit (Norgen). Examples of the refolding treatment are a method for adding arginine, Tween 80, sodium acetate and DL-cystine to the solubilized solution and a method using TAPS-sulfonate (Katayama Chemical., Ltd.) or Refolding CA Kit (Takara Bio Inc.)

In this regard, the polypeptide having the coiled-coil forming unit and Stx2eB are joined to form the fusion protein of the invention, and they may be joined chemically. In this case, in one method, the polypeptide having the coiled-coil forming unit and Stx2eB are expressed individually and then joined using a cross-linker.

When the polypeptide having the coiled-coil forming unit and Stx2eB are expressed individually, the respective DNA sequences can be obtained by chemical synthesis, the DNA fragments can be amplified by a known gene amplification method using the DNA sequences as the templates, and the respective expression plasmids can be constructed according to the above method. Each expression plasmid can be introduced into the host as described above and each target protein can be obtained.

When the polypeptide having the coiled-coil forming unit and Stx2eB are joined using a cross-linker, amino groups and thiol groups (SH groups) in the proteins, aldehyde groups of sugar chains in the proteins and the like can be used, although the functional groups to be used are not limited. For example, in one method, the SH groups of the polypeptide having the coiled-coil forming unit and the amino groups of Stx2eB are reacted, and more specifically, the polypeptide which has been reduced using a reducing agent such as dithiothreitol (DTT) and Stx2eB to which pyridyl disulfide groups have been introduced by N-succinyl-3-(2-pyridyldithio) proprionate (SPDP) may be incubated and thus joined. In addition, polypeptide having the coiled-coil forming unit and Stx2eB may be joined chemically using bonding through use of interactions between the biomolecules such as biotin and avidin.

The fusion protein and its multimer obtained by the above methods can be further isolated and purified by general purification means. Here, as the purification means, purification methods such as affinity chromatography, ion-exchange chromatography, hydrophobic interaction chromatography and gel filtration chromatography are mentioned.

The invention includes a vaccine against porcine edema disease containing the fusion protein and/or the fusion protein multimer of the invention as an active ingredient. It is preferable that the vaccine of the invention contains the fusion protein multimer. A dimer, a trimer, a tetramer, a pentamer or a higher multimer or a mixture of the multimers is preferable.

The vaccine against porcine edema disease preferably contains 0.1 to 1000 μg of the fusion protein and/or the fusion protein multimer in a dosage. Moreover, when a susceptible animal is immunized with the vaccine, toxin-neutralizing antibodies of the level to defend against the onset or higher can be induced.

The vaccine of the invention may contain a pharmaceutically acceptable carrier. Examples are saline, buffered saline, dextrose, water, glycerol, an isotonic aqueous buffer and a combination thereof. In addition, additives such as an adjuvant, an emulsifying agent, a preservative, a tonicity agent and a pH adjusting agent may be appropriately added.

As the adjuvant, Emulsigen (MVP Laboratories), tocopherol acetate, alum, saponin (QS21, ISCOM), CpG oligo and the like are included.

An antigen which prevents an infectious disease in swine may be added to the vaccine of the invention in addition to the fusion protein. Examples of the infectious disease are porcine parvovirus infection, swine erysipelas, transmissible gastroenteritis in swine, swine mycoplasma pneumonia, porcine atrophic rhinitis, Japanese encephalitis in swine, porcine circovirus infection, porcine reproductive and respiratory syndrome, streptococcal infection in swine, swine influenza, porcine pleuropneumonia, Glasser's disease, swine dysentery, porcine epidemic diarrhea, *E. coli* infection in swine, proliferative enteropathy, necrotizing enterocolitis in swine, porcine salmonellosis and porcine rotavirus infection.

The vaccine of the invention may be administered through any administration pathway such as transdermal administration, sublingual administration, ophthalmic administration, intradermal administration, intramuscular administration, oral administration, enteral administration, nasal administration, intravenous administration, subcutaneous administration, intraperitoneal administration and inhalational administration from the mouth to the lung.

By inoculating pigs with the vaccine of the invention, the vaccine induces potent toxin-neutralizing antibodies and can prevent the onset of porcine edema disease effectively. It is inferred that the reason for this is that when Stx2eB and the polypeptide capable of forming a coiled-coil structure are fused, the original appropriate conformation of Stx2eB including the pentamer formation is easily achieved.

The invention includes a kit for measuring the amount of antibodies to Stx2eB in a sample, wherein the kit contains the fusion protein and/or the fusion protein multimer. The kit containing the fusion protein of the invention may be a plate on which the fusion protein is immobilized. A sample is added to the plate, and the fusion protein on the plate and antibodies contained in the sample are reacted. Secondary antibodies labelled with an enzyme or a fluorescent substance are added and reacted with the primary antibodies. The amount of antibodies contained in the sample may be measured by adding a substrate of the enzyme if necessary and detecting the product of the enzyme reaction or the fluorescent intensity. The kit of the invention may be used to assess the efficacy of a vaccine by immunizing a pig with the vaccine containing the fusion protein and/or the fusion protein multimer as an active ingredient and then detecting the production of antibodies derived from the vaccine.

The invention includes a DNA vaccine against porcine edema disease containing the nucleic acid fragment or the recombinant expression vector as an active ingredient. In the DNA vaccine of the invention, the nucleic acid fragment or the recombinant expression vector preferably contains a promoter sequence for expressing the fusion protein after immunizing a pig.

With respect to the method for producing the DNA vaccine of the invention, challenge test is conducted in pigs with STEC or Stx2e before and after inoculating the pigs with the DNA vaccine. As a result, a nucleic acid fragment or a recombinant expression vector which has significantly reduced a clinical symptom of porcine edema disease is selected as an active ingredient of an agent for treating porcine edema disease, and the active ingredient amount may be determined from the dosage at this point.

The DNA vaccine of the invention may contain a pharmaceutically acceptable carrier. Examples are saline, buffered saline, dextrose, water, glycerol, an isotonic aqueous buffer and a combination thereof. In addition, additives such as an adjuvant, an emulsifying agent, a preservative, a tonicity agent and a pH adjusting agent may be appropriately added.

The DNA vaccine of the invention may be administered through any administration pathway such as transdermal administration, sublingual administration, ophthalmic administration, intradermal administration, intramuscular administration, oral administration, enteral administration, nasal administration, intravenous administration, subcutaneous administration, intraperitoneal administration and inhalational administration from the mouth to the lung.

The invention includes an antibody which binds to the fusion protein and/or the fusion protein multimer. Monoclonal and polyclonal antibodies or the like can be produced or a human antibody thereof can be produced, using the fusion protein and/or the fusion protein multimer of the invention as the antigen, by a general immunization method (Current Protocols in Molecular Biology, Antibody Engineering: A PRACTICAL APPROACH, Edited by J. McCAFFERTY et al., or ANTIBODY ENGINEERING second edition, Edited by Carl A. K. BORREBAECK). An antibody which binds to the fusion protein and/or its multimer can be produced by an antibody production method using phage display technique (Phage Display of Peptides and Proteins: A Laboratory Manual, Edited by Brian K. Kay et al., Antibody Engineering: APRACTICAL APPROACH, Edited by J. McCAFFERTY et al., or ANTIBODY ENGINEERING second edition, Edited by Carl A. K. BORREBAECK). The antibody of the invention is supposed to be used as an agent for treating porcine edema disease, a kit and a carrier for affinity chromatography, which are explained below.

The invention includes an agent for treating porcine edema disease containing the antibody as an active ingredient. With respect to the method for producing the therapeutic agent of the invention, challenge test is conducted in pigs with STEC or Stx2e before and after inoculating the pigs with the antibody produced by the above method. As a result, an antibody which has significantly reduced a clinical symptom of porcine edema disease is selected as an active ingredient of the agent for treating porcine edema disease, and the active ingredient amount may be determined from the antibody dosage at this point.

The agent for treating porcine edema disease of the invention contains the antibody as an active ingredient and may contain a pharmaceutically acceptable carrier. Examples are saline, buffered saline, dextrose, water, glycerol, an isotonic aqueous buffer and a combination thereof. In addition, additives such as an adjuvant, an emulsifying agent, a preservative, a tonicity agent and a pH adjusting agent may be appropriately added.

The agent for treating porcine edema disease of the invention may be administered through any administration pathway such as transdermal administration, sublingual administration, ophthalmic administration, intradermal administration, intramuscular administration, oral administration, enteral administration, nasal administration, intravenous administration, subcutaneous administration, intraperitoneal administration and inhalational administration from the mouth to the lung.

The invention includes a kit for measuring the Stx2eB content in a sample, wherein the kit contains the antibody which binds to the fusion protein and/or the fusion protein multimer. As such a kit, a kit in which the antibody which binds to the fusion protein is immobilized on a plate or the like is included. The kit containing the antibody of the invention may be used to assess whether a subject is infected with porcine edema disease or not, using the Stx2eB content as an index. For example, a sample is added to the plate on which the antibody is immobilized, and then antibodies labelled with an enzyme or a fluorescent dye are added. The Stx2eB content in the sample can be measured by incubating and washing the plate, adding a chromogenic substrate if necessary and measuring the fluorescent intensity.

Examples of the plate are Nunc Immuno plate MaxiSorp (Thermo scientific), a plate for ELISA (Sumitomo Bakelite Co., Ltd.), ELISPOT (MERCK), Immuno plate (Cosmo Bio Co., ltd.), ELISA plate (IWAKI) and ELISA plate (ExtraGene), and the antibody may be immobilized on the plate by a method which is generally employed by one skilled in the art.

Examples of the method for labelling the antibody with an enzyme or a fluorescent dye are EasyLink antibody conjugation kits (abcam), Lightning-Link Rapid Conjugation System (Innova Biosciences Ltd), Oyster Antibody Labeling Kit (Luminartis GmbH), enzyme labelling kit EZ-Link (PIERCE Biotechnology), PlatinumLink Protein Labeling Kit (Kreatech Biotechnology BV) and DyLight Antibody Labeling Kit (PIERCE Biotechnology).

The invention includes a carrier for affinity chromatography in which the antibody to the fusion protein and/or the fusion protein multimer is bound to a carrier. The fusion protein and/or the fusion protein multimer of the invention is expressed in or outside the host, and when expressed in the host, the fusion protein and/or the fusion protein multimer is recovered by breaking the host, while when expressed outside the host, the fusion protein and/or the fusion protein multimer is recovered from the culture surroundings. The carrier of the invention is supposed to be used for recovering the fusion protein and/or the fusion protein multimer from such a contaminant fraction or the like.

Examples of the carrier are HiTrap NHS-activated HP (GE Healthcare), NHS-activated Sepharose 4 Fast Flow (GE Healthcare), CNBr-activated Sepharose 4B (GE Healthcare), CNBr-activated Sepharose 4 Fast Flow (GE Healthcare), EAH Sepharose 4B (GE Healthcare), ECH Sepharose 4B (GE Healthcare), Profinity epoxy resin (BIORAD) and Affi-Gel Hz Hydrazide gel (BIORAD), and the antibody may be bound by a method which is generally used by one skilled in the art.

EXAMPLES

The invention is further explained in detail with Examples below, but the invention is not limited by these Examples.

Example 1

Preparation of Stx2eB-His-COMP Protein and its Multimer (1) Construction of Expression Vector Construction of Stx2eB-His-Expressing Vector and Preparation of Stx2eB-His-Expressing *E. coli*

A DNA sequence (SEQ ID NO:2) was designed based on a DNA sequence encoding an Stx2eB precursor (SEQ ID NO:1) by optimizing the codons for expression in *E. coli* and yeast and adding the recognition sequence for restriction enzyme Nde I to the 5' end and the recognition sequence for restriction enzyme Xho I to the 3' end for inserting into an expression vector, and the DNA fragment was artificially synthesized. The synthetic DNA and plasmid pET-22b (Merck KGaA) were treated with Nde I and Xho I and joined. The joined product was introduced into *E. coli* DH5α, and the plasmid obtained was named "an intermediate vector 1".

PCR reaction was conducted using the intermediate vector 1 as the template and oligo DNA containing the recognition sequence for restriction enzyme Nco I (SEQ ID NO:3) and oligo DNA containing the recognition sequence for restriction enzyme Xho I (SEQ ID NO:4) as the primers, and DNA encoding mature Stx2eB containing no secretory signal sequence was amplified.

The amplified product and plasmid pET-21d (Merck KGaA) were treated with Nco I and Xho I and joined. The joined product was introduced into *E. coli* DH5α, and the plasmid obtained was named pSTXB. The plasmid expresses a fusion protein of Stx2eB and His-tag (hereinafter referred to as Stx2eB-His) (SEQ ID NO:5) (FIG. 1). A DNA nucleotide sequence encoding Stx2eB-His is shown in SEQ ID NO:6. *E. coli* BL21 (DE3) (Merck KGaA) was transfected with pSTXB, and an *E. coli* STXB strain expressing Stx2eB-His was obtained.

(2) Construction of Stx2eB-His-COMP-Expressing Vector and Preparation of Stx2eB-His-COMP-Expressing *E. coli*

PCR reaction was conducted using pB (NPL 5, Infect Immun. 2005, 7, 5654-65), which is an expression vector of a Cholera toxin B subunit precursor, as the template and oligo DNA containing the recognition sequence for restriction enzyme Mun I (SEQ ID NO:7) and oligo DNA containing the recognition sequence for restriction enzyme Mun I and a sequence encoding a $(GP)_2GH_6$(EcoR I)$H_6$ linker (an artificial sequence) (SEQ ID NO:8) as the primers, and DNA encoding CTB-$(GP)_2GH_6$(EcoRI) $H_6$ was amplified.

The amplified DNA was treated with Mun I and a pPIC3.5K vector (Life Technologies) was cut with EcoR I, and the DNA and the pPIC3.5K vector were joined. The joined product was introduced into *E. coli* DH5α, and the plasmid obtained was named "an intermediate vector 2".

DNA (SEQ ID NO:11) which encodes a fusion protein of DNA encoding a $(G_4S)_3$ linker (an artificial sequence) (SEQ ID NO:9) and DNA encoding the pentamer-forming domain of cartilage oligomeric matrix protein (hereinafter referred to as COMP) with codons optimized for expression in *E. coli* and yeast (SEQ ID NO:10) was designed and artificially synthesized. PCR reaction was conducted using the synthetic DNA as the template and oligo DNA containing the recognition sequence for restriction enzyme Mun I (SEQ ID NO:12) and oligo DNA containing the recognition sequence for restriction enzyme EcoR I (SEQ ID NO:13) as the primers, and DNA encoding $(G_4S)_3$-linker-COMP was amplified. The amplified product which was treated with Mun I and EcoR I and the intermediate vector 2 which was treated with EcoR I were joined. The joined product was introduced into *E. coli* DH5α, and the plasmid obtained was named "an intermediate vector 3".

PCR reaction was conducted using the intermediate vector 3 as the template and oligo DNA containing the recognition sequence for restriction enzyme Xho I (SEQ ID NO:14) and oligo DNA containing the recognition sequence for restriction enzyme Xho I (SEQ ID NO:15) as the primers, and DNA encoding a fusion protein of a $(GP)_2GH_6$ $(G_4S)_3$ linker and COMP was amplified. The amplified DNA and pSTXB were treated with Xho I and joined. The joined product was introduced into *E. coli* DH5α, and the plasmid obtained was named pSTXC. The plasmid is a vector for expressing a fusion protein of Stx2eB, the $(GP)_2GH_6(G_4S)_3$ linker and COMP (hereinafter referred to as Stx2eB-His-COMP) (SEQ ID NO:16) (FIG. 2). A DNA nucleotide sequence encoding Stx2eB-His-COMP is shown in SEQ ID NO:17. *E. coli* BL21 (DE3) strain was transfected with pSTXC, and an *E. coli* STXC strain expressing Stx2eB-His-COMP was obtained.

(3) Construction of Stx2eB-His-COMP-His-Z-Expressing Vector and Preparation of Stx2eB-His-COMP-His-Z-Expressing *E. coli*

A COMP-His-Z-expressing vector (NPL 6, Infect. Immune. 2011, 79(10), 4260-4275) was cut with Nco I and Xho I, and a DNA fragment encoding a fusion protein of COMP, a $(GP)_2G_4SH_6G_4S(GP)_2$ linker and immunoglobulin-binding domain Z (hereinafter referred to as domain Z) (the fusion protein is referred to as COMP-His-Z below) was prepared. The DNA fragment and a pET-21d vector (MERCK) which was treated with restriction enzymes Nco I and Xho I were joined. The joined product was introduced into *E. coli* DH5α, and the plasmid obtained was named "an intermediate vector 4". The intermediate vector 4 was further treated with Nco I and Bsm I, and "an intermediate vector 5" in which the sequence from the 5' end of COMP to the recognition site for Bsm I was removed was prepared.

Next, PCR reaction was conducted using pSTXC as the template and the oligo DNA of SEQ ID NO:3 and SEQ ID NO:15 as the primers, and DNA encoding Stx2eB-His-COMP was amplified. The amplified DNA was treated with restriction enzymes Nco I and Bsm I. The DNA fragment lacks a part of the carboxyl-terminus of COMP. The DNA fragment and the intermediate vector 5 were joined. The joined product was introduced into *E. coli* DH5α, and the plasmid obtained was named pSTXZ. The plasmid expresses a fusion protein of Stx2eB, the $(GP)_2GH_6(G_4S)_3$ linker, COMP, the $(GP)_2G_4SH_6G_4S(GP)_2$ linker and the domain Z (hereinafter referred to as Stx2eB-His-COMP-His-Z) (SEQ ID NO:18) (FIG. 4). A DNA sequence encoding Stx2eB-His-COMP-His-Z is shown in SEQ ID NO:19. *E. coli* BL21 (DE3) (MERCK) was transfected with pSTXZ, and an *E. coli* STXZ strain expressing Stx2eB-His-COMP-His-Z was obtained.

Example 2

Cultivation of Recombinant *E. coli* and Purification of Expressed Proteins (1) Cultivation of Strain STXB and Purification of Stx2eB-His To a 12 mL test tube, 3 mL of a 2×YT culture medium and an ampicillin solution (final concentration of 200 μg/mL) were added, and the strain STXB was inoculated, followed by culturing at 37° C. with shaking for about 16 hours (preculture). To a 2 L conical flask, 200 mL of a 2×YT culture medium and an ampicillin solution (final concentration of 200 μg/mL) were added, and 2 mL of the preculture solution was inoculated, followed by culturing at 37° C. with shaking until the $OD_{590}$ exceeded 0.5. When the $OD_{590}$ of the culture exceeded 0.5, isopropyl-β-D-thiogalactopyranoside (IPTG) was added to give a final concentration of 10 μM, and the solution was cultured at 25° C. with shaking for 20 hours. The culture solution was transferred to a centrifuge tube, and the bacterial cells were recovered by centrifugation at 10,000 rpm at 4° C. for 10 minutes. The inclusion body fraction was prepared by centrifugation using BugBuster (Merck KGaA) from the bacterial cells recovered.

The inclusion body fraction prepared was solubilized with a 1% SDS solution, and the buffer was replaced with PBS by dialysis (Spectrum laboratories, inc. Spectra/Por CE dialysis membrane. MWCO: 3.5-5 kD), thereby obtaining an Stx2eB-His antigen.

(2) Cultivation of Strain STXC and Purification of Stx2e-His-COMP

To a 12 mL test tube, 3 mL of a 2×YT culture medium and an ampicillin solution (final concentration of 200 μg/mL) were added, and the strain STXC was inoculated, followed by culturing at 37° C. with shaking for about 16 hours (preculture). To a 2 L conical flask, 200 mL of a 2×YT culture medium and an ampicillin solution (final concentration of 200 μg/mL) were added, and 2 mL of the preculture solution was inoculated, followed by culturing at 37° C. with shaking until the $OD_{590}$ exceeded 0.5. When the $OD_{590}$ of the culture exceeded 0.5, isopropyl-β-D-thiogalactopyranoside (IPTG) was added to give a final concentration of 10 μM, and the solution was cultured at 37° C. with shaking for six hours. The culture solution was transferred to a centrifuge tube, and the bacterial cells were recovered by centrifugation at 10,000 rpm at 4° C. for 10 minutes. The inclusion body fraction was prepared by centrifugation using BugBuster (Merck KGaA) from the bacterial cells recovered.

Next, a 6M guanidine hydrochloride (pH 8.2) solution was added to the inclusion bodies, and a solubilized solution was prepared. The solubilized solution was subjected to refolding treatment referring to PTL 1 (JP-A-2008-50344). Specifically, Tween 80 (final concentration of 0.05%), sodium acetate (final concentration of 1 M) and DL-cystine (final concentration of 2 mM) were added to the solubilized solution and the mixture was left still at 4° C. overnight. After the refolding treatment, Stx2eB-His-COMP was purified using His Trap HP (GE Healthcare Japan Corporation), and the buffer was replaced with PBS by ultrafiltration (Amicon Ultra-15 30 kDa, Millipore Corporation), thereby obtaining an Stx2eB-His-COMP antigen. SDS-PAGE was conducted under a non-reducing condition using a 12.5% acrylamide gel, and formation of multimers was confirmed by CBB staining and western blotting using an anti-His antibody (FIG. 3).

(3) Cultivation of Strain STXZ and Purification of Stx2e-His-COMP-His-Z

To a 12 mL test tube, 3 mL of a 2×YT culture medium and an ampicillin solution (final concentration of 200 μg/mL) were added, and the strain STXZ was inoculated, followed by culturing at 37° C. with shaking for about 16 hours (preculture). To a 2 L conical flask, 200 mL of a 2×YT culture medium and an ampicillin solution (final concentration of 200 μg/mL) were added, and 2 mL of the preculture solution was inoculated, followed by culturing at 37° C. with shaking until the $OD_{590}$ exceeded 0.5. When the $OD_{590}$ of the culture exceeded 0.5, IPTG was added to give a final concentration of 10 μM, and the solution was cultured at 37° C. with shaking for six hours. The culture solution was transferred to a centrifuge tube, and the bacterial cells were recovered by centrifugation at 10,000 rpm at 4° C. for 10 minutes. The inclusion body fraction was prepared by centrifugation using BugBuster (MERCK) from the bacterial cells recovered.

Next, a 6M guanidine hydrochloride (pH 8.2) solution was added to the inclusion bodies, and a solubilized solution was prepared. The solubilized solution was subjected to refolding treatment referring to PTL 1 (JP-A-2008-50344). Specifically, Tween 80 (final concentration of 0.05%), sodium acetate (final concentration of 1 M) and DL-cystine (final concentration of 2 mM) were added to the solubilized solution and the mixture was left still at 4° C. overnight. After the refolding treatment, Stx2eB-His-COMP-His-Z was purified using His Trap HP (GE Healthcare), and the buffer was replaced with PBS by ultrafiltration (Amicon Ultra-15 30 kDa, Millipore Corporation), thereby obtaining an Stx2e-His-COMP-His-Z antigen. SDS-PAGE was conducted under a non-reducing condition using a 5 to 20% acrylamide gel, and formation of multimers was confirmed by CBB staining and western blotting using an anti-His antibody (FIG. 5).

Example 3

1. Confirmation of Induction of Neutralizing Antibodies in Mice (1) Preparation of Vaccines and Immunization of Mice a. Comparison of Neutralizing Antibody-Inducing Capacities Between Stx2eB-His Antigen and Stx2eB-His-COMP Antigen A vaccine in which 50 μg of the Stx2eB-His-COMP antigen and 50 μL of Imject Alum (registered trademark) (Thermo Fisher Scientific Inc.) were mixed per 100 μL was prepared. Because the amount of Stx2eB-His which is equivalent to 50 μg of Stx2eB-His-COMP in terms of mole is 26.6 μg, a vaccine in which 26.6 μg of the Stx2eB-His antigen and 50 μL of Imject Alum (registered trademark) were mixed per 100 μL was prepared. In addition, by mixing and emulsifying 50 μg of the Stx2e-His-COMP antigen and 50 μL of Incomplete Freund's Adjuvant (Nippon Becton Dickinson Company, Ltd.) per 100 μL, a vaccine was prepared.

The vaccines were injected subcutaneously in an amount of 100 μL to female seven-week-old BALB/c mice (five mice per group) three times at two-week intervals. Blood was collected two weeks after the third immunization, and the antibody titers were measured by the Stx2e neutralization test using Vero cells below.

b. Comparison of Neutralizing Antibody-Inducing Capacities Between Stx2eB-His-COMP Antigen and Stx2eB-His-COMP-His-Z Antigen A vaccine in which 50 μg of the Stx2eB-His-COMP antigen and 50 μL of Imject Alum (registered trademark) were mixed per 100 μL was prepared. Because the amount of Stx2eB-His-COMP-His-Z which is equivalent to 50 μg of Stx2eB-His-COMP in terms of mole is 75 μg, a vaccine in which 75 μg of the Stx2eB-His-COMP-His-Z antigen and 50 μL of Imject Alum (registered trademark) were mixed per 100 μL was prepared.

The vaccines were injected subcutaneously in an amount of 100 μL to female seven-week-old BALB/c mice (five mice per group) three times at two-week intervals. Blood was collected two weeks after the third immunization, and the antibody titers were measured by the Stx2e neutralization test using Vero cells below.

(2) Preparation of Toxin Solution

A loopful of a glycerol stock of edema bacterium isolated from a pig was inoculated on a Circlegrow (MP Biomedicals) agar medium and cultured at 37° C. overnight. A single colony was inoculated in a 500 mL conical flask containing 50 mL of a Circlegrow culture medium and cultured at 37° C. with rotating at 220 rpm overnight. The culture solution (5 mL) was inoculated in four 500 mL conical flasks containing 50 mL of a Circlegrow culture medium and cultured at 37° C. with rotating at 220 rpm for eight hours. The culture solutions were pooled and the absorbance ($OD_{650}$) was measured. After centrifugation at 10000 g at 4° C. for 15 minutes, the precipitates were collected. The precipitates were suspended in 20 mL of 10 mM Tris-HCl (7.0). Ultrasonic treatment (Branson, Duty Cycle 30%, Output 1) was conducted until the absorbance ($OD_{650}$) decreased to 60% of the value before the treatment. After centrifugation at 10000 g at 4° C. for 30 minutes, the supernatant was collected. The supernatant was sterilized by filtration through a 0.22 μm filter. The sample was frozen and stored at −80° C.

(3) Measurement of Cytotoxic Activities

<Materials>

Cells: Vero cells

Culture medium for cultivation: 5% FBS-added Eagle's culture medium (10% TPB, 1.5% sodium bicarbonate, 0.1% PS)

Culture medium for dilution: Eagle's culture medium (10% TPB, 1.5% sodium bicarbonate, 0.1% PS)

<Preparation of Cell Suspension>

Vero cells were cultured in the culture medium for cultivation, and the supernatant was removed. Per middle-size square (75 $cm^2$), 3 mL of trypsin-EDTA was added, and the treatment was conducted at 37° C. for 5 to 10 minutes. After adding 10 mL of the culture medium for cultivation, the cells were separated by pipetting and collected in a centrifuge tube. The cells were recovered by centrifugation at 1500 rpm for five minutes. The cells were resuspended in 5 mL of the culture medium for cultivation, and the number of the cells was counted. The concentration was adjusted to $4.0\times10^5$ cells/mL using the culture medium for cultivation.

<Measurement of Cytotoxic Activity>

The culture medium for dilution was dispensed to a 96-well plate for cell cultivation in an amount of 125 μl/well. Two-fold serial dilutions of the toxin solution, which were diluted with the culture medium for dilution, were added thereto in an amount of 25 μl/well. The cell suspension adjusted to $4.0\times10^5$ cells/mL was added in an amount of 50 μL/well. The plate was sealed and cultured at 37° C. for five days.

<Assessment>

The cell-sheet formation percentage of the negative control was confirmed to be 95% or more, and the dilution showing a cell-sheet formation percentage of 50% or less was determined to be the 50% cytotoxic activity (cytotoxic dose, $CD_{50}$) amount.

(4) Stx2e Neutralization Test Using Vero Cells

<Materials>

Cells: Vero cells

Culture medium for cultivation: 5% FBS-added Eagle's culture medium (10% TPB, 1.5% sodium bicarbonate, 0.1% PS)

Culture medium for dilution: Eagle's culture medium (10% TPB, 1.5% sodium bicarbonate, 0.1% PS)

<Preparation of Cell Suspension>

After Vero cells were cultured in the culture medium for cultivation, the supernatant of the cells was removed. Per middle-size square (75 $cm^2$), 3 mL of trypsin-EDTA was added, and the treatment was conducted at 37° C. for 5 to 10 minutes. After adding 10 mL of the culture medium for cultivation, the cells were separated by pipetting and collected in a centrifuge tube. The cells were recovered by centrifugation at 1500 rpm for five minutes. The cells are resuspended in 5 mL of the culture medium for cultivation, and the number of the cells is counted. The concentration was adjusted to $4.0\times10^5$ cells/mL using the culture medium for cultivation.

<Neutralization>

The toxin solution (60 μL) which was adjusted to 10 $CD_{50}$ with the culture medium for dilution and 60 μL of two-fold serial dilutions of a serum sample diluted with the culture medium for dilution were mixed and reacted at 37° C. for one hour. The culture medium for dilution was dispensed to a 96-well plate in an amount of 100 μl/well. The neutralization solutions reacted at 37° C. were added each in an amount of 50 μL. The cell suspension adjusted to $4.0\times10^5$ cells/mL was added in an amount of 50 μL/well. The plate was sealed and cultured at 37° C. for five days.

<Assessment>

The cell-sheet formation percentage of the negative control was confirmed to be 95% or more, and the highest dilution of the serum sample showing a cell-sheet formation percentage of 50% or more was determined to be the neutralizing antibody titer. The results are shown in Table 1 and Table 2.

TABLE 1

Comparison of Neutralizing Antibody-Inducing Capacities between Stx2eB-His Antigen and Stx2eB-His-COMP Antigen

| Antigen | Adjuvant | Individual No. 1 | 2 | 3 | 4 | 5 |
|---|---|---|---|---|---|---|
| Placebo (PBS) | ImjectAlum | <1 | <1 | <1 | <1 | <1 |
| Stx2eB-His | ImjectAlum | <1 | <1 | <1 | <1 | <1 |
| Stx2eB-His-COMP | ImjectAlum | >64 | >64 | 32 | 32 | 8 |
| Stx2eB-His-COMP | IFA | >64 | >64 | >64 | 8 | 16 |

TABLE 2

Comparison of Neutralizing Antibody-Inducing Capacities between Stx2eB-His-COMP Antigen and Stx2eB-His-COMP-His-Z Antigen

| Antigen | Adjuvant | Individual No. 1 | 2 | 3 | 4 | 5 |
|---|---|---|---|---|---|---|
| Placebo (PBS) | ImjectAlum | <2 | <2 | <2 | <2 | <2 |
| Stx2eB-His-COMP | ImjectAlum | >128 | 16 | >128 | >128 | >128 |
| Stx2eB-His-COMP-Z | ImjectAlum | 8 | 32 | 4 | 16 | 32 |

From these results, it was confirmed that the Stx2eB-His-COMP antigen induces neutralizing antibodies to Stx2e in mice. On the other hand, the increase in the neutralizing antibodies was not observed in the Stx2eB-His injection group. The results of this study show that an appropriate multimer structure is difficult to be formed by Stx2eB alone, and the fusion with COMP is advantageous. Moreover, it was confirmed that the Stx2eB-His-COMP antigen can induce significantly potent toxin-neutralizing antibodies compared to the Stx2eB-His-COMP-His-Z antigen.

2. Stx2e Challenge Test in Mice

A vaccine in which 50 μg of the Stx2e-His-COMP antigen and 50 μL of Incomplete Freund's Adjuvant (Nippon Becton Dickinson Company, Ltd.) were mixed per 100 μL and emulsified was prepared. Female seven-week-old BALB/c mice were subjected to the test, and 100 μL of the vaccine was injected subcutaneously three times at two-week intervals (10 mice per group). Two weeks after the third immunization, 0.4 mL (32000 50% Vero cell degeneration amount) of a toxin solution prepared from edema bacterium (the preparation method is described above) was injected intraperitoneally. The mice were observed for seven days after the Stx2e administration, and the number of deaths was counted. The results are shown in Table 3.

TABLE 3

| Group | Number of Mice | Number of Survivors | Survival Rate (%) |
|---|---|---|---|
| Placebo (PBS) | 10 | 4 | 40 |
| Stx2eB-His-COMP | 10 | 10 | 100 |

From Table 3, a significant difference (p=0.0041) was observed between the placebo group and the immunized group, and it was confirmed that immunization of mice with the Stx2eB-His-COMP antigen defends against the Stx2e challenge.

Example 4

Confirmation of Induction of Neutralizing Antibodies in Pigs

A vaccine containing 100 μg of the Stx2eB-His-COMP antigen and 0.4 mL of Emulsigen (MVP Laboratories) per 2 mL was prepared. The vaccine was injected intramuscularly to three- to four-week-old pigs in the cervical region twice at a two-week interval. Blood was collected at the time of the first immunization, at the time of the additional immunization and two weeks after the additional immunization, and the antibody titers were measured by the Stx2e neutralization test using Vero cells. The results are shown in Table 4.

TABLE 4

| Group | Individual No. | First Immunization | Additional Immunization | Two Weeks After Additional Immunization |
|---|---|---|---|---|
| Placebo | 1 | <2 | <2 | <20 |
| (PBS) | 2 | <2 | <2 | <20 |
| Stx2eB- | 3 | <2 | 8 | <20 |
| His- | 4 | <2 | <2 | 20 |
| COMP | 5 | <2 | 8 | 40 |
| | 6 | <2 | 8 | 80 |
| | 7 | 2 | 2 | 80 |

From these results, it was confirmed that the Stx2eB-His-COMP antigen induces neutralizing antibodies to Stx2e also in pigs.

Example 5

Stx2e Challenge Test in Pigs

To the pigs used in Example 4, 20 mL (600000 50% Vero cell degeneration amount) of a toxin solution prepared from edema bacterium (the preparation method is described above) was injected intraperitoneally two weeks after the additional immunization. Moreover, to exclude the influence of LPS mixed, an Stx2e solution which was heated at 80° C. for 10 minutes to thermally inactivate Stx2e was administered to one pig in the placebo group. The clinical symptoms were observed for three days after the Stx2e administration. The results are shown in Table 5.

TABLE 5

| Group | Individual No. | At Challenge Neutralizing Antibody Titer | Toxin Heating | Three-Day Observation After Challenge |
|---|---|---|---|---|
| Placebo (PBS) | 1 | <20 | Not heated | Dead on the next day of the challenge |
| | 2 | <20 | Heated | Without abnormalities |
| Stx2eB- | 3 | <20 | Not heated | Without abnormalities |
| His- | 4 | 20 | Not heated | Without abnormalities |
| COMP | 6 | 80 | Not heated | Without abnormalities |

From the results in Table 5, it was confirmed that immunization of pigs with the Stx2eB-His-COMP antigen can defend against the Stx2e challenge.

Example 6

Preparation of Stx2eB-His-CMP Protein and its Multimer (1) Construction of Stx2eB-His-CMP-Expressing Vector and Preparation of Stx2eB-His-CMP-Expressing *E. coli*

Figure 6:
FIG. 6 A schematic diagram of Stx2eB-His-CMP.

A DNA sequence (SEQ ID NO:36) was designed by optimizing the codons (SEQ ID NO:34) for expressing a fusion protein of Stx2eB, a $(GP)_2GH_6(G_4S)_3$ linker and CMP (hereinafter referred to as Stx2eB-His-CMP) (SEQ ID NO:35) (FIG. 6) in *E. coli*, adding the recognition sequence for restriction enzyme Nco I to the 5' end and the recognition sequence for restriction enzyme XhoI to the 3' end for inserting into an expression vector and further adding protective nucleotides to the 5' end and the 3' end, and the DNA sequence was artificially synthesized. The synthetic DNA was inserted into the Eco RV site of plasmid pUC57 (GenScript Corporation). The joined product was introduced into *E. coli* DH5α, and the plasmid obtained was named "an intermediate vector 6".

The intermediate vector 6 was treated with Nco I and Xho I, and a DNA fragment encoding Stx2eB-His-CMP was obtained. The DNA fragment and plasmid pET-21d (Merck KGaA) which was treated with Nco I and Xho I were joined. The joined product was introduced into *E. coli* DH5α, and the plasmid obtained was named pSTX-CMP. Furthermore, pSTX-CMP was introduced into *E. coli* BL21 (DE3) (Merck KGaA), and an *E. coli* STX-CMP strain expressing Stx2eB-His-CMP was obtained.

(2) Cultivation of Strain STX-CMP and Preparation of Stx2e-His-CMP Antigen

To a 12 mL test tube, 3 mL of a 2×YT culture medium and an ampicillin solution (final concentration of 200 μg/mL) were added, and the strain STX-CMP was inoculated, followed by culturing at 37° C. with shaking for about 16 hours (preculture). To a 2 L conical flask, 200 mL of a 2×YT culture medium and an ampicillin solution (final concentration of 200 μg/mL) were added, and 2 mL of the preculture solution was inoculated, followed by culturing at 37° C. with shaking until the $OD_{590}$ exceeded 0.5. When the $OD_{590}$ of the culture exceeded 0.5, isopropyl-β-D-thiogalactopyranoside (IPTG) was added to give a final concentration of 10 μM, and the solution was cultured at 37° C. with shaking for six hours. The culture solution was transferred to a centrifuge tube, and the bacterial cells were recovered by centrifugation at 10,000 rpm at 4° C. for 10 minutes. The bacterial cells in 100 mL of the culture solution were suspended in a lysis buffer (50 mM Tris-HCl (pH8.0), 500 mM NaCl) containing lysozyme (final concentration of 1 mg/mL), and the bacterial cells were disrupted by Ultrasonic Disrupter UD-201 (Tomy Co., Ltd.). The disrupted bacterial cell solution was centrifuged at 10,000 rpm at 4° C. for 10 minutes, and inclusion bodies were obtained. The inclusion bodies were resuspended in the lysis buffer to wash the inclusion bodies, and the inclusion bodies were collected by centrifugation at 10,000 rpm at 4° C. for 10 minutes.

Figure 7:
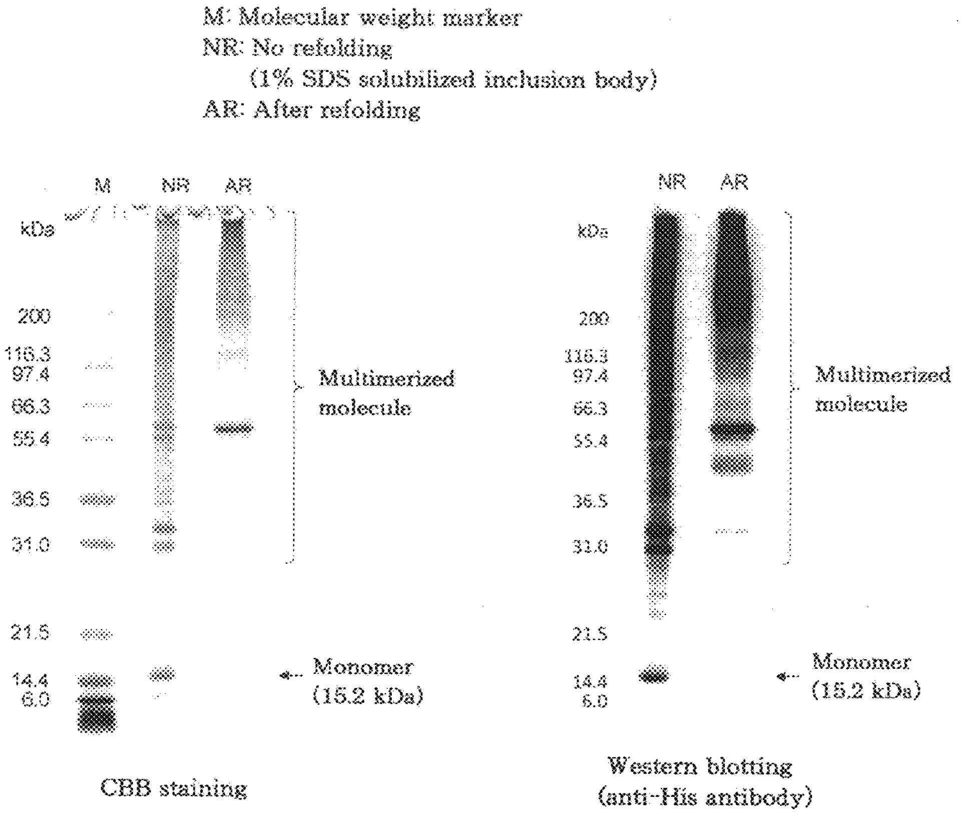
FIG. 7 A figure showing the formation of multimers of Stx2eB-His-CMP observed.

Next, a buffer containing 50 mM tris (pH 8.2) and 6 M guanidine hydrochloride was added to the inclusion bodies, and a solubilized solution was prepared. The solubilized solution was subjected to refolding treatment by stepwise dialysis. Specifically, the solubilized solution was dialyzed for four hours using a buffer containing 50 mM tris (pH 8.2) and 2 M guanidine hydrochloride, then dialyzed for four hours using a buffer containing 50 mM tris (pH 8.2), 1 M guanidine hydrochloride, 1 M arginine hydrochloride and 5 mM DL-cystine, then dialyzed for 16 hours using a buffer containing 50 mM tris (pH 8.2), 0.5 M guanidine hydrochloride, 1 M arginine hydrochloride and 5 mM DL-cystine and finally dialyzed for four hours using a PBS buffer containing 1 M arginine hydrochloride. The sample obtained here was used as an Stx2eB-His-CMP antigen. SDS-PAGE was conducted under a non-reducing condition using a 12.5% acrylamide gel, and formation of multimers was confirmed by CBB staining and western blotting using an anti-His antibody (FIG. 7).

Example 7

Stx2e Challenge Test in Mice (1) Preparation of Vaccine

Because the amount of Stx2eB-His-CMP which is equivalent to 50 μg of Stx2eB-His-COMP described in Example 3 in terms of mole is 46.5 μg, vaccine in which 46.5 μg of the Stx2eB-His-CMP antigen and 50 μL of Incomplete Freund's Adjuvant (Nippon Becton Dickinson Company, Ltd.) were mixed per 100 μL and emulsified was prepared.

(2) Stx2e Challenge Test in Mice

Female nine-week-old BALB/c mice (10 mice per group) were subjected to the test. The vaccine in an amount of 100 μL was injected subcutaneously to the immunized group twice at a two-week interval. Nothing was administered to the non-administration group. Two weeks after the second immunization, 0.4 mL (64000 50% Vero cell degeneration amount) of an Stx2e toxin solution prepared from edema bacterium (the preparation method is described above) was injected intraperitoneally. The mice were observed for seven days after the Stx2e administration, and the number of deaths was counted. The results are shown in Table 6.

TABLE 6

| Group | Number of Mice | Number of Survivors | Survival Rate (%) |
|---|---|---|---|
| Non-administration | 10 | 1 | 10 |
| Stx2eB-His-CMP | 10 | 5 | 50 |

From Table 6, a significant difference ($p=0.047$) was observed between the non-administration group and the immunized group, and it was confirmed that immunization of mice with the Stx2eB-His-CMP antigen protects a half of the mice from the Stx2e challenge.

INDUSTRIAL APPLICABILITY

It is possible to prevent the onset of porcine edema disease in farms where the onset of porcine edema disease is anticipated.

The invention claimed is:

1. A fusion protein comprising (i) a polypeptide having a coiled-coil forming unit joined to (ii) a B subunit of Shiga toxin Stx2e (Stx2eB), wherein the fusion protein does not comprise an immunoglobulin binding domain Z.

2. The fusion protein of claim 1, wherein the polypeptide (i) and the B subunit (ii) are joined by a linker sequence and/or a tag sequence between the polypeptide (i) and the B subunit (ii).

3. The fusion protein of claim 1, wherein the coiled-coil forming unit is derived from a natural multimer-forming protein.

4. The fusion protein of claim 3, wherein the natural multimer-forming protein is selected from the group consisting of cartilage oligomeric matrix protein (COMP), cartilage matrix protein (CMP), tetrabrachion (TB) and GCN4.

5. The fusion protein of claim 4, wherein the natural multimer-forming protein is COMP or CMP.

6. The fusion protein of claim 5, wherein the natural multimer-forming protein is COMP.

7. The fusion protein of claim 6 which is a polypeptide comprising the amino acid sequence represented by SEQ ID NO:27 or SEQ ID NO:28, or a polypeptide comprising the amino acid sequence represented by SEQ ID NO:27 or SEQ ID NO:28 with deletion, substitution or insertion of one or several amino acid residues.

8. The fusion protein of claim 5, wherein the natural multimer-forming protein is CMP.

9. The fusion protein of claim 8 which is a polypeptide comprising the amino acid sequence represented by SEQ ID NO:32 or SEQ ID NO:33, or a polypeptide comprising the amino acid sequence represented by SEQ ID NO:32 or SEQ ID NO:33 with deletion, substitution or insertion of one or several amino acid residues.

10. The fusion protein of claim 1, wherein the Stx2eB is a polypeptide comprising the amino acid sequence represented by SEQ ID NO:20, SEQ ID NO:22 or SEQ ID NO:24, or a polypeptide comprising the amino acid sequence represented by SEQ ID NO:20, SEQ ID NO:22 or SEQ ID NO:24 with deletion, substitution or insertion of one or several amino acid residues.

11. A vaccine against porcine edema disease comprising the fusion protein of claim 1 as an active ingredient.

12. A method for producing a fusion protein multimer, comprising: expressing a fusion protein comprising (i) a polypeptide having a coiled-coil forming unit joined to (ii) a B subunit of Shiga toxin Stx2e (Stx2eB) wherein the fusion protein does not comprise an immunoglobulin binding domain Z in a host, and then refolding the fusion protein.

13. The method of claim 12, wherein the fusion protein has a spacer between the polypeptide and the B subunit.

14. The method of claim 12, wherein the polypeptide has a coiled-coil forming unit derived from a natural multimer-forming protein which is selected from the group consisting of cartilage oligomeric matrix protein (COMP), cartilage matrix protein (CMP), tetrabrachion (TB) and GCN4.

15. The method of claim 14, wherein the polypeptide has a coiled-coil forming unit derived from COMP or CMP.

16. The method of claim 15, wherein the polypeptide has a coiled-coil forming unit derived from COMP.

17. The method of claim 16, wherein the polypeptide is a polypeptide comprising the amino acid sequence represented by SEQ ID NO:27 or SEQ ID NO:28, or a polypeptide comprising the amino acid sequence represented by SEQ ID NO:27 or SEQ ID NO:28 with deletion, substitution or insertion of one or several amino acid residues.

18. The method of claim 15, wherein the polypeptide has a coiled-coil forming unit derived from CMP.

19. The method of claim 18, wherein the polypeptide is a polypeptide comprising the amino acid sequence represented by SEQ ID NO:32 or SEQ ID NO:33, or a polypeptide comprising the amino acid sequence represented by SEQ ID NO:32 or SEQ ID NO:33 with deletion, substitution or insertion of one or several amino acid residues.

20. The method of claim 12, wherein the Stx2eB is a polypeptide comprising the amino acid sequence represented by SEQ ID NO:20, SEQ ID NO:22 or SEQ ID NO:24, or a polypeptide comprising the amino acid sequence represented by SEQ ID NO:20, SEQ ID NO:22 or SEQ ID NO:24 with deletion, substitution or insertion of one or several amino acid residues.

* * * * *